(12) United States Patent
Stefanchik et al.

(10) Patent No.: US 9,247,997 B2
(45) Date of Patent: Feb. 2, 2016

(54) PATIENT-REFERENCED SURGICAL SUPPORT FRAME

(75) Inventors: David Stefanchik, Morrow, OH (US); Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 276 days.

(21) Appl. No.: 13/249,883

(22) Filed: Sep. 30, 2011

(65) Prior Publication Data
US 2013/0085342 A1 Apr. 4, 2013

(51) Int. Cl.
*A61B 1/32* (2006.01)
*A61B 19/00* (2006.01)
*A61B 17/34* (2006.01)
*A61B 17/00* (2006.01)

(52) U.S. Cl.
CPC .......... *A61B 19/26* (2013.01); *A61B 17/3417* (2013.01); *A61B 2017/00535* (2013.01); *A61B 2017/00876* (2013.01); *A61B 2017/00991* (2013.01); *A61B 2017/347* (2013.01); *A61B 2017/3447* (2013.01)

(58) Field of Classification Search
CPC .... A61B 1/313; A61B 1/3132; A61B 1/3135; A61B 1/317; A61B 2017/3445; A61B 2017/3447; A61B 1/32; A61B 2017/3464–2017/3466; A61B 2017/347; A61B 17/3462
USPC .............. 600/201–249; 606/53–60, 1, 96, 98, 606/108, 130, 114, 115
See application file for complete search history.

(56) References Cited

U.S. PATENT DOCUMENTS

| | | | | |
|---|---|---|---|---|
| 4,895,141 A | * | 1/1990 | Koeneman et al. | 606/54 |
| 4,920,959 A | * | 5/1990 | Witzel et al. | 606/53 |
| 5,375,588 A | * | 12/1994 | Yoon | 600/114 |
| 5,810,712 A | * | 9/1998 | Dunn | 600/114 |
| 6,110,182 A | * | 8/2000 | Mowlai-Ashtiani | 606/130 |
| 6,217,577 B1 | * | 4/2001 | Hofmann | 606/57 |

(Continued)

FOREIGN PATENT DOCUMENTS

| | | |
|---|---|---|
| DE | 203 03 643 U1 | 7/2003 |
| DE | 10 2006 013982 A1 | 9/2007 |

(Continued)

OTHER PUBLICATIONS

International Search Report for Application No. PCT/US2012/056864, issued Feb. 1, 2013. (7 pages).

*Primary Examiner* — Eduardo C Robert
*Assistant Examiner* — Michelle C Eckman
(74) *Attorney, Agent, or Firm* — Nutter McClennen & Fish LLP

(57) ABSTRACT

A patient-referenced surgical support frame and method of use are provided. In one embodiment, a surgical support frame can have at least three support members coupled by adjustable linkages. Each support member can have a lumen extending therethrough for receiving a cannula, and each support member can be configured such that the at least three support members (or the cannulas extending therethrough) are angularly adjustable relative to one another, and such that a distance between each of the at least three support members is adjustable. In use, the surgical support frame can be positioned on a skin surface of a patient and used to retain one or more instruments extending through the support members in a fixed orientation or position with respect to the patient, thereby allowing more than two instruments to be used simultaneously.

13 Claims, 29 Drawing Sheets

(56) References Cited

U.S. PATENT DOCUMENTS

| | | | |
|---|---|---|---|
| 6,663,616 B1 * | 12/2003 | Roth et al. | 606/1 |
| 7,588,571 B2 * | 9/2009 | Olsen | 606/57 |
| 7,695,480 B2 * | 4/2010 | Solar et al. | 606/130 |
| 7,918,826 B2 | 4/2011 | Armstrong et al. | |
| 8,366,710 B2 * | 2/2013 | Hirata et al. | 606/57 |
| 2006/0235405 A1 * | 10/2006 | Hawkes | 606/69 |
| 2007/0106305 A1 * | 5/2007 | Kao et al. | 606/130 |
| 2008/0108998 A1 * | 5/2008 | Lindemann | 606/71 |
| 2009/0018401 A1 * | 1/2009 | Kim | 600/231 |
| 2009/0137877 A1 * | 5/2009 | Minnelli et al. | 600/204 |
| 2009/0221966 A1 | 9/2009 | Richard | |
| 2009/0306679 A1 * | 12/2009 | Murphy | 606/130 |
| 2010/0228092 A1 * | 9/2010 | Ortiz et al. | 600/204 |
| 2010/0228094 A1 * | 9/2010 | Ortiz et al. | 600/205 |
| 2012/0259204 A1 * | 10/2012 | Carrat et al. | 600/414 |
| 2012/0316575 A1 * | 12/2012 | Farin et al. | 606/130 |

FOREIGN PATENT DOCUMENTS

| | | |
|---|---|---|
| EP | 1 520 544 A1 | 4/2005 |
| EP | 2 329 787 A2 | 6/2011 |
| WO | 98/10822 A1 | 3/1998 |
| WO | 2009/035663 A2 | 3/2009 |
| WO | 2011/043644 A1 | 4/2011 |

* cited by examiner

FIGURE 2a
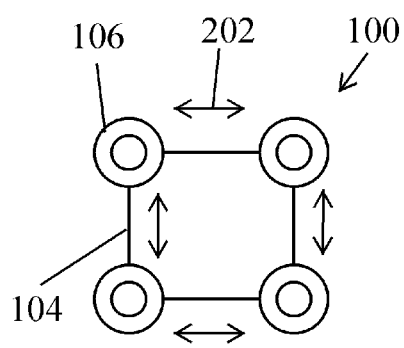
FIGURE 2b
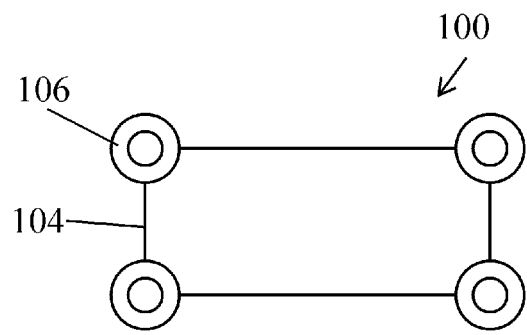
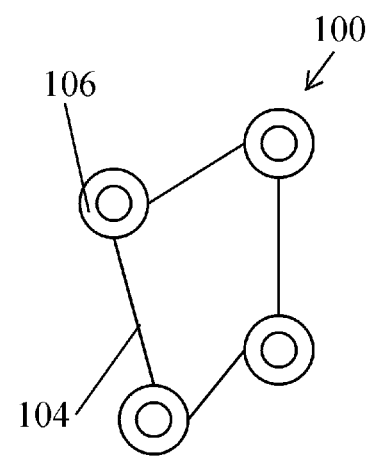
FIGURE 2c
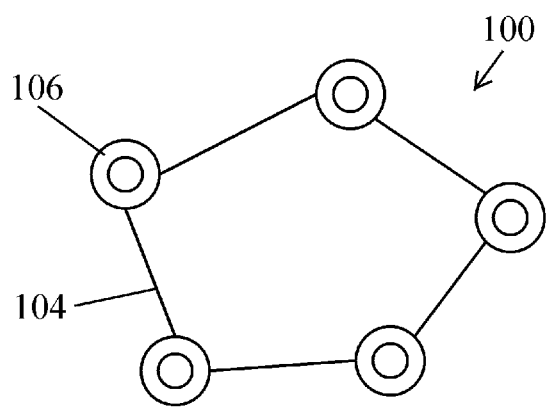
FIGURE 2d

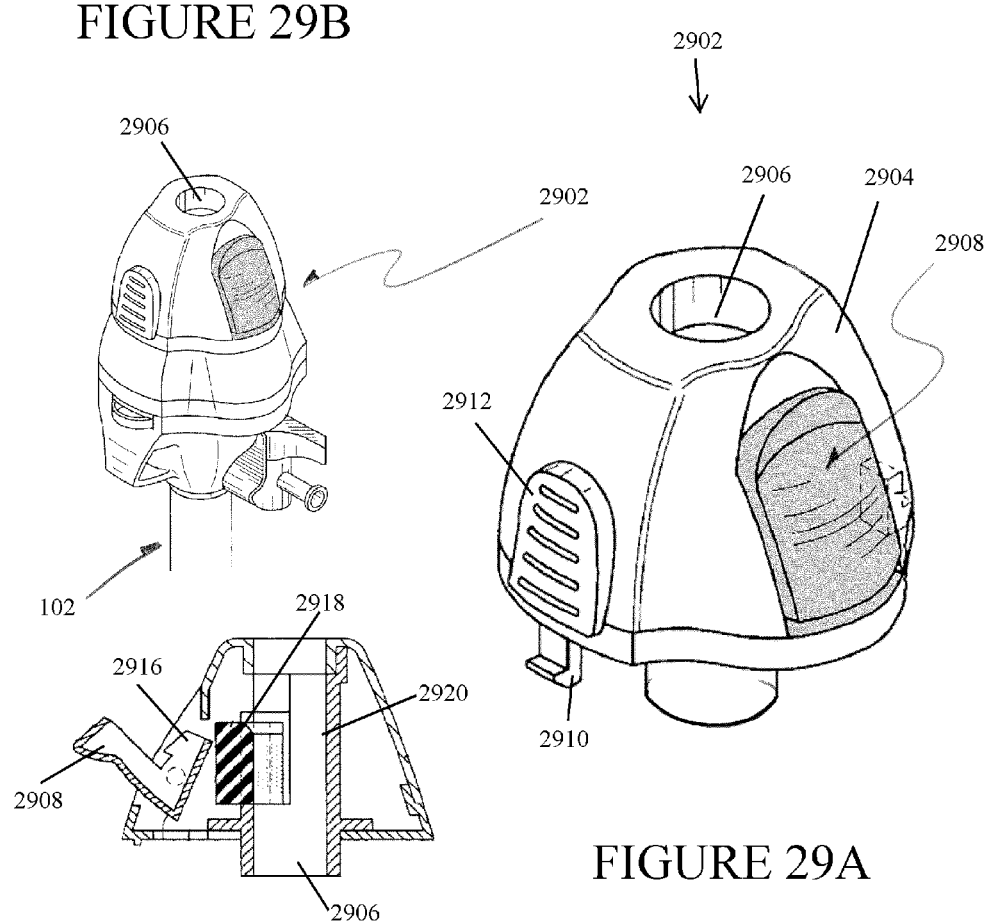

PATIENT-REFERENCED SURGICAL SUPPORT FRAME

FIELD

This invention is related to surgical tools for use in laparoscopic surgery and, in particular, to a patient-referenced surgical support frame and methods for use to orient and retain multiple surgical instruments in a desired position.

BACKGROUND

During laparoscopic surgery, a small incision is formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs.

Many laparoscopic procedures require the use of multiple tools simultaneously or in rapid succession, so oftentimes more than one incision is formed and a trocar is placed through each incision. Each trocar, however, is independent of any other trocar and must be held in position throughout the surgery. Releasing a trocar, or the instrument inserted therethrough, allows the trocar and instrument to fall out of position. As a result, surgeons are limited to controlling no more than two trocars or surgical instruments at any time, and any other trocars or surgical instruments must be removed or held by an additional surgeon or assistant.

Accordingly, there is a need in the art for devices and methods for retaining multiple trocars and surgical instruments in relation to both each other and a patient undergoing surgery.

SUMMARY

The present invention generally provides a patient-referenced surgical support frame and methods of use for retaining multiple trocars and/or surgical instruments in relation to both each other and a patient. The devices and methods of the present invention allow a surgeon to effectively position and control multiple surgical instruments by retaining each instrument in a fixed position and/or orientation when not in use by the surgeon.

In one embodiment, a surgical support frame is provided including at least three support members connected to one another by at least two adjustable linkages. Each support member has a lumen extending therethrough for receiving a cannula (e.g., a cannula at a distal end of a trocar or other surgical access device). Each support member is also configured such that a cannula extending through one of the at least three support members is angularly adjustable relative to a cannula extending through another one of the at least three support members. In addition, a distance between each of the at least three support members is adjustable.

As a result, the surgical support frame can provide polyaxial freedom of movement for one or more cannulas extending therethrough. This can be accomplished in a variety of manners, including, for example, by providing for polyaxial angular adjustment of a support member having a cannula extending therethrough. In other embodiments, the support member can be rigidly or pivotably fixed to the adjustable linkages and can include a mechanism to receive a cannula and provide for polyaxial angular adjustment of the cannula with respect to the support member.

The surgical support frame of the present invention can have any number of modifications or additional features. For example, in some embodiments, the surgical support frame can include at least three adjustable linkages that can be arranged to define a perimeter of an enclosed shape. By way of further example, in some embodiments, the at least three support members can include first, second, and third support members, and the adjustable linkages can be arranged to define a perimeter of a triangle. In other embodiments, the at least three support members can include first, second, third, and fourth support members, and the adjustable linkages can be arranged to define a perimeter of a square (or other quadrilateral, e.g., a rectangle, etc.).

In certain embodiments, the surgical support frame of the present invention can also include a locking mechanism associated with at least one of the at least three support members for locking at least one of the at least three support members such that a cannula extending through one of the at least three support members is retained in a desired angular orientation relative to a cannula extending through another one of the at least three support members.

The support members can be attached to the adjustable linkages in a variety of manners. For example, in some embodiments, the support members and adjustable linkages can be connected using ball-and-socket joints that permit polyaxial adjustment of the support member. In such embodiments, the locking mechanism can be configured to restrain the movement of the ball-and-socket joints to retain the support member (and any cannula extending therethrough) in a particular orientation.

In certain other embodiments, the support members can be fixedly or pivotably (e.g., providing only two-dimensional adjustment) attached to the adjustable linkages and can include a separate mechanism for providing polyaxial angular adjustment of a cannula or trocar extending through the support member. This can be accomplished in a variety of manners including, for example, a ball-and-socket joint in which the ball contains a lumen to receive a cannula or trocar and enable polyaxial adjustment with respect to a socket formed in the support member. In such embodiments, the locking mechanism can be configured to prevent this adjustment and/or translation of the cannula or trocar extending through the support member.

In still other embodiments, the adjustable linkages of the surgical support frame can also include a locking mechanism associated with at least one of the at least two adjustable linkages for locking at least one of the at least two adjustable linkages at a desired length.

In another aspect of the invention, a surgical method is provided including positioning at least three support members on a skin surface of a patient where the at least three support member are connected to one another by a plurality of adjustable linkages. The method further includes moving one of the at least three support members to adjust an effective length of at least one of the plurality of adjustable linkages connected thereto. The method also includes angularly orienting a cannula extending through one of the at least three support members to pivot at least a portion of the support member relative to at least one of the plurality of adjustable linkages connected thereto.

In some embodiments, a cannula can be mounted in each support member such that a distal end of each cannula extends through the skin surface and into a body cavity of the patient.

In certain other embodiments, the method can further include inserting an instrument through the cannula and locking the support member in a fixed position such that the support member retains the cannula and the instrument inserted therethrough in a fixed position.

In certain other embodiments, the method can also include locking at least one of the adjustable linkages at a desired length.

In another aspect of the invention, a surgical method is provided including manipulating a first surgical instrument extending through a first cannula mounted on a support frame resting on a skin surface of a patient to position a distal end of the first surgical instrument at a desired location within a body cavity of the patient. The method can also include manipulating a second surgical instrument extending through a second cannula mounted on the support frame to position a distal end of the second surgical instrument at a desired location with a body cavity of the patient. Still further, the method can include locking at least one of the first and second cannulas in a fixed orientation relative to the support frame such that the distal end of at least one of the first and second surgical instruments is maintained in a desired fixed position, and manipulating a third surgical instrument extending through a third cannula mounted on the support frame to position a distal end of the third surgical instrument at a desired location within a body cavity of the patient.

In some embodiments, the support frame can include a plurality of adjustable linkages connecting the first, second, and third cannulas, and manipulating at least one of the first, second, and third surgical instruments can cause at least one of the plurality of adjustable linkages to move such that a distance between any two of the cannulas is adjusted.

In some other embodiments, manipulating the third surgical instrument can be done with at least one of the first and second cannulas locked in a fixed orientation.

Still further, in certain embodiments, the method can include manipulating a fourth surgical instrument extending through a fourth cannula mounted on the support frame to position a distal end of the fourth surgical instrument at a desired location within a body cavity of the patient.

Using the teachings of the present invention, surgeons involved in laparoscopic procedures can more quickly and efficiently control and position multiple surgical instruments extending into a body cavity of a patient at multiple locations. The surgical support frame of the present invention is able to aid the surgeon by providing a frame of reference for each surgical instrument fixed to the patient and related to each other instrument in use. As a result, the frame can maintain each instrument in a fixed position and/or orientation with respect to both the patient and each other instrument in use.

BRIEF DESCRIPTION OF THE DRAWINGS

The invention will be more fully understood from the following detailed description taken in conjunction with the accompanying drawings, in which:

FIG. 2a is a top view illustration of one embodiment of a surgical support frame including four support members;

FIG. 2b is a top view illustration of an alternative embodiment of a surgical support frame including four support members;

FIG. 2c is a top view illustration of another embodiment of a surgical support frame including four support members;

FIG. 2d is a top view illustration of one embodiment of a surgical support frame including five support members.

FIG. 19B is an exploded view of the support member assembly of FIG. 19A;

FIG. 29A is a perspective view of an instrument locking member of the present invention;

FIG. 29B is a perspective view of the instrument locking member in FIG. 29A disposed on the proximal end of a trocar; and FIG. 29C is a cross-sectional view of the instrument locking member in FIG. 29A.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
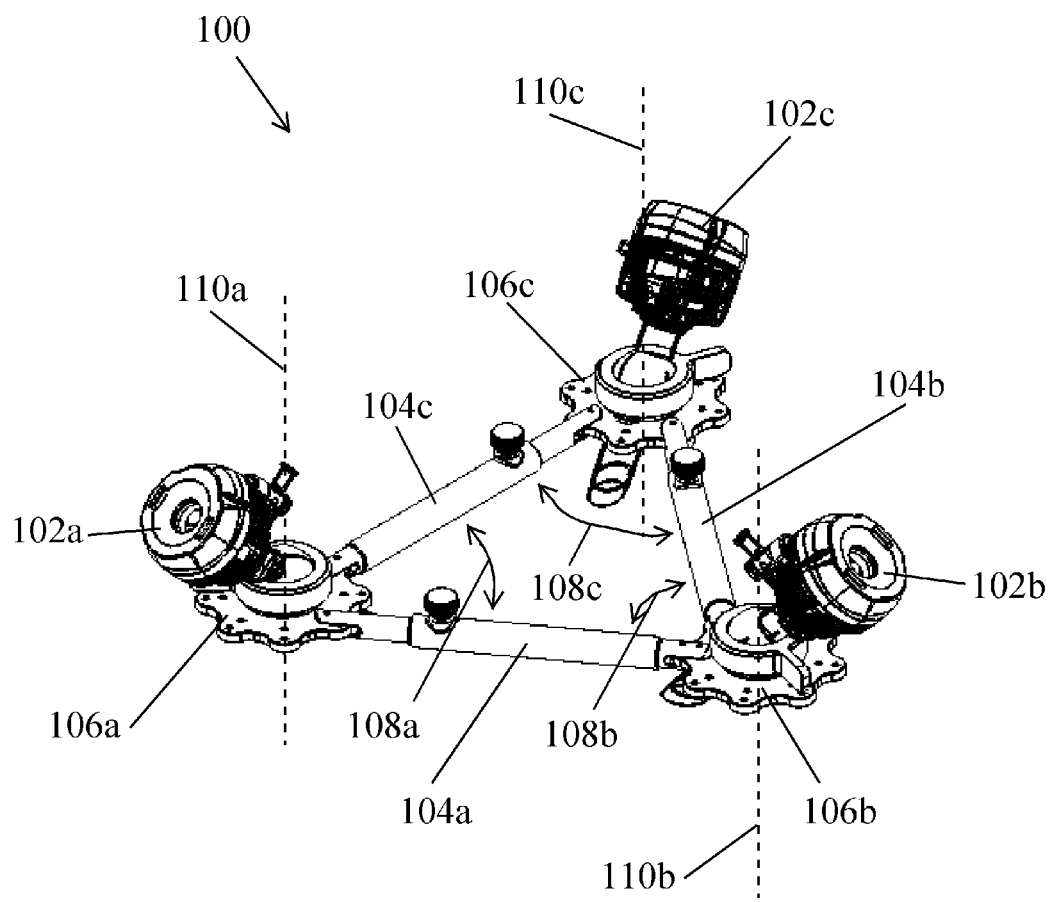
FIG. 1 is a top perspective view of one embodiment of a surgical support frame supporting three trocars.

In one aspect of the invention, a surgical support frame is provided that can be used during a laparoscopic procedure to retain one or more surgical instruments in a particular position and/or orientation with respect to a patient. One embodiment of a surgical support frame of the present invention is illustrated in FIG. 1. As shown, the surgical support frame 100 can be configured to hold one or more cannulas (e.g., cannulas of trocars 102) in a particular orientation with respect to the other cannula(s) and with respect to the patient.

The frame 100 can be configured to be placed on a skin surface of a patient. For example, the surgical support frame 100 can be placed on top of a patient's torso when the patient is lying supine on a gurney. As a result, the frame is not only able to hold each cannula in a desired position and/or orientation with respect to any other cannula, but also with respect to the body of the patient.

Referring to FIG. 1, the surgical support frame includes three adjustable linkages 104a, 104b, 104c and three support members 106a, 106b, 106c. Two or more support members are preferred to ensure that the surgical support frame rests on the body of a patient in a stable position. Each support member 106a-c can be movably connected to the other support members by one or more of the plurality of adjustable linkages 104a-c. As shown, the first support member 106a is connected to the second support member 106b by the first adjustable linkage 104a, the second support member 106b is connected to the third support member 106c by the second adjustable linkage 104b, and the third support member 106c is connected to the first support member 106a by the third adjustable linkage 104c. As a result of these connections, the surgical support frame 100 defines an enclosed shape, e.g., a triangle in the illustrated embodiment. Moreover, the connections allow both the angular relation and the distance between each of the support members to be adjusted.

By way of example, FIGS. 2a-d illustrate the surgical support frame 100 having additional support members and linkages arranged to define various enclosed shapes. For example, the surgical support frame 100 of FIG. 2a is arranged to form a square (i.e., each adjustable linkage 104 has the same length and the angle between each adjustable linkage connected to a support member 106 is 90 degrees). Each adjustable linkage 104 can, however, be adjusted in length, as shown by double arrows 202. In FIG. 2b, the adjustable linkages 104 are not equal in length and the surgical support frame 100 forms a rectangular shape. In addition to changing length, the angular orientation of the adjustable linkages 104 can also be adjusted, as shown in FIG. 2c. Moreover, FIG. 2d illustrates an embodiment of a surgical support frame 100 having five support members 106 and five adjustable linkages 104. One skilled in the art will appreciate that the surgical support frame can be created using any number of support members and adjustable linkages, and that the number of support members and adjustable linkages need not be identical (e.g., an adjustable linkage can be added as a diagonal cross-member to the surgical support frame of FIG. 2b, resulting in some support members being connected to more than two adjustable linkages).

Still further, the surgical support frame 100 can provide for polyaxial angular adjustment of a cannula extending through a support member 106a-c. FIG. 1 illustrates the various degrees of freedom provided by the surgical support frame 100. For example, and as described above, the angular orientation between the adjustable linkages 104a-c can be adjusted as shown by angular adjustment indicators 108a, 108b, 108c. Each support member 106a-c can also include features to allow angular adjustment of a cannula extending therethrough about a central axis 110a, 110b, 110c of the support member 106a-c. In addition, each cannula 102a, 102b, 102c extending through a support member 106a-c can translate along its own axis through the support member 106a-c. Accordingly, the surgical support frame 100 provides polyaxial angular adjustment of cannulas 102a-c in relation to each other, the support frame, and the patient.

Figure 3:
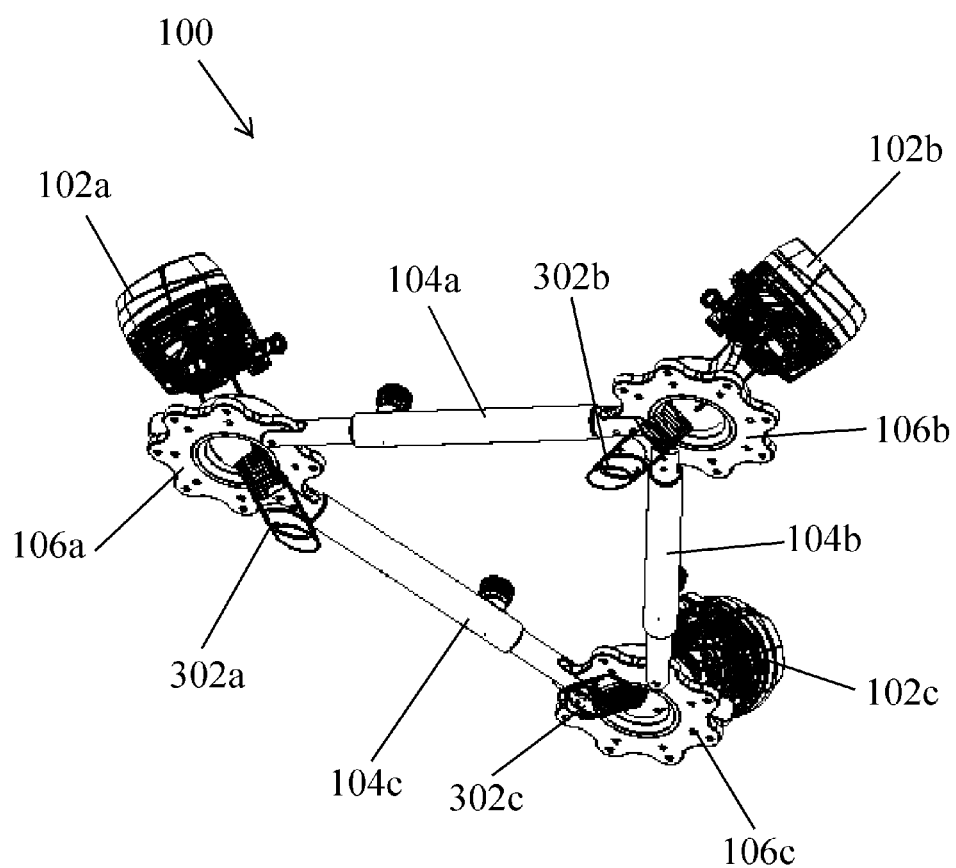
FIG. 3 is a bottom perspective view of the surgical support frame of FIG. 1.
Figure 4:
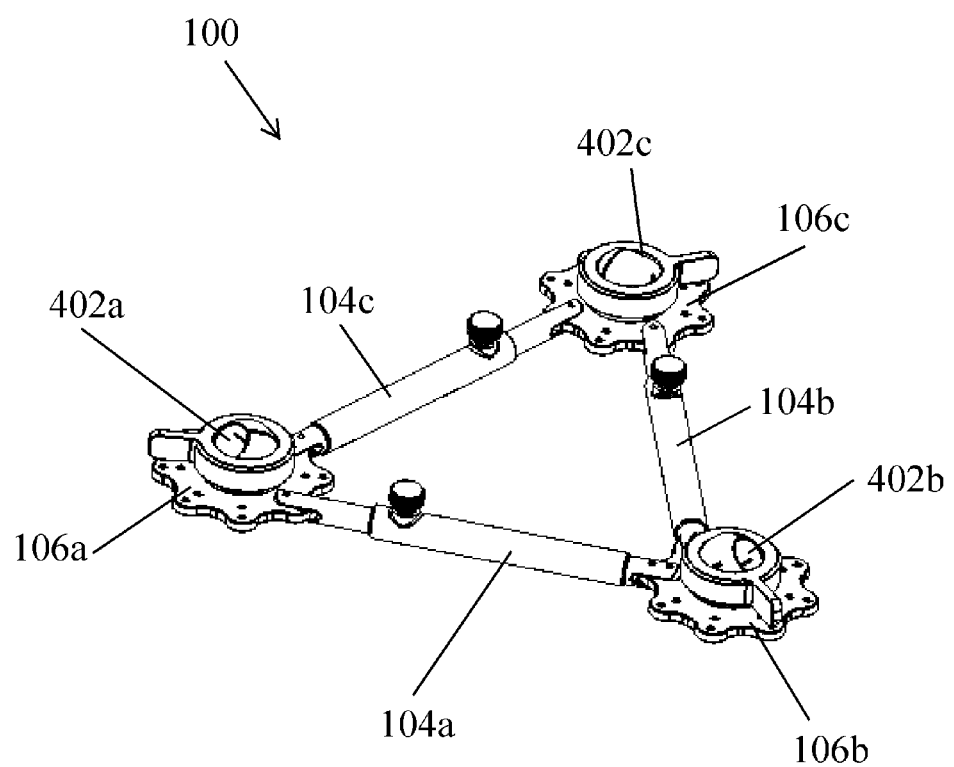
FIG. 4 is a top perspective view of the surgical support frame of FIG. 1, shown without any trocars.

FIGS. 3 and 4 show alternate views of the surgical support frame 100 shown in FIG. 1. As shown in FIG. 3, each support member 106a-c has a lumen extending therethrough for receiving a cannula, such as a trocar cannula 302a, 302b, 302c on the distal end of a trocars 102a-c. A person skilled in the art will appreciate that a variety of trocars and other surgical access devices can be used with the surgical support frame of the present invention. An exemplary trocar is disclosed in U.S. Pat. No. 7,918,826 to Armstrong et al. entitled "Trocar Assembly," the teachings of which are hereby incorporated by reference in its entirety. The lumen 402a, 402b, 402c that each trocar 102a-c extends through is shown in more detail in FIG. 4, which illustrates the surgical support frame 100 without any trocars 102a-c.

Figure 5:
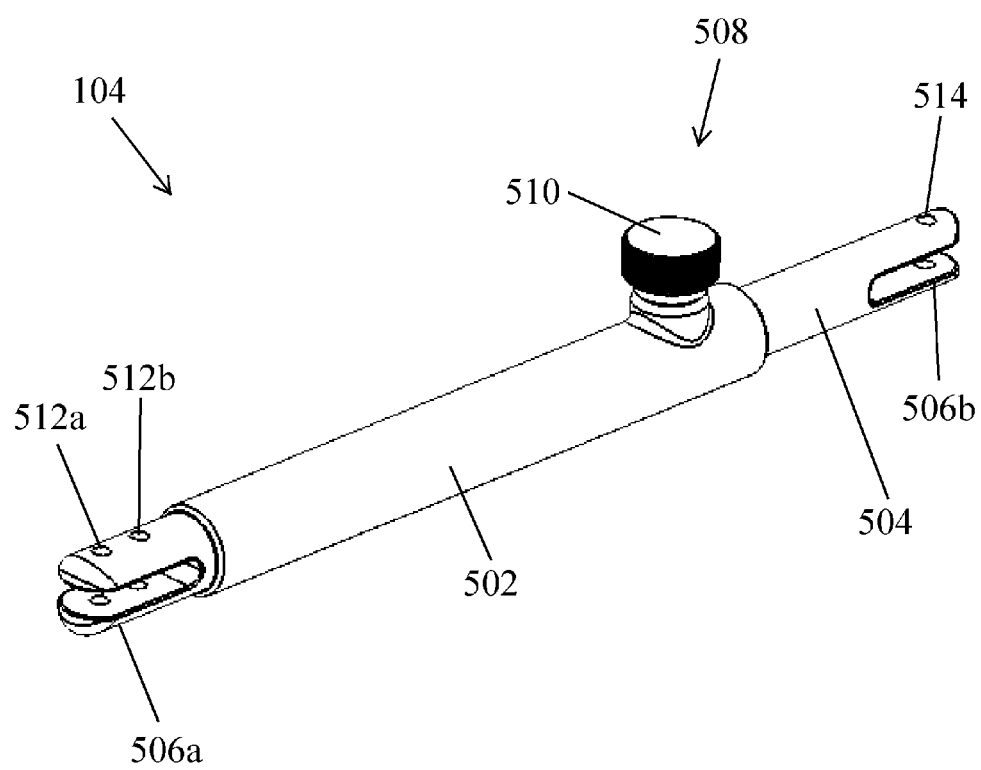
FIG. 5 is a perspective view of one of the adjustable linkages of the surgical support frame of FIG. 1.
Figure 6:
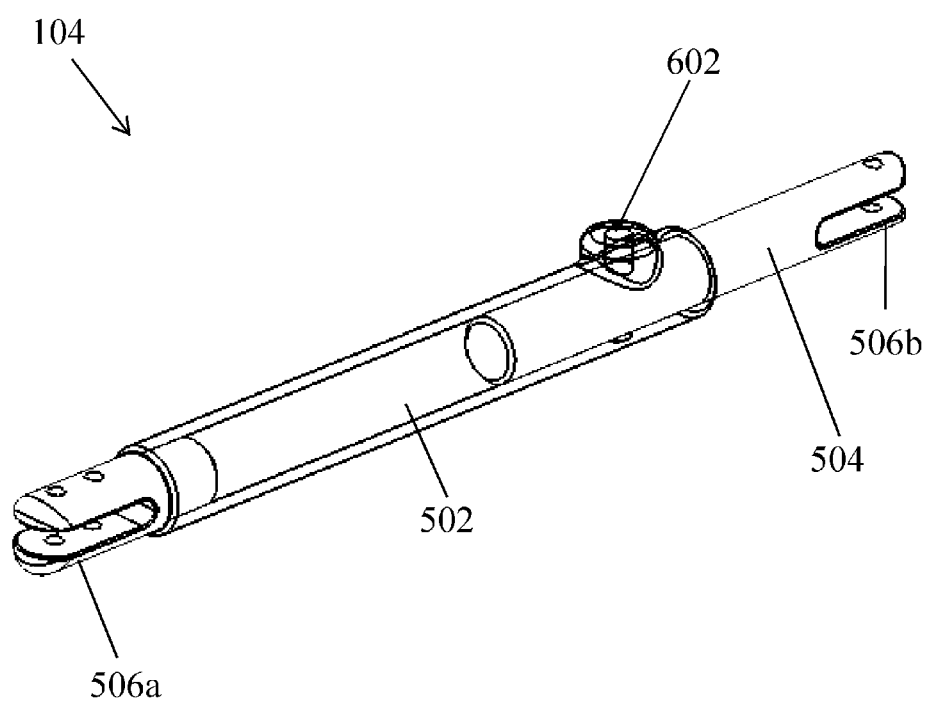
FIG. 6 is a transparent view of the adjustable linkage of FIG. 5.
Figure 7:
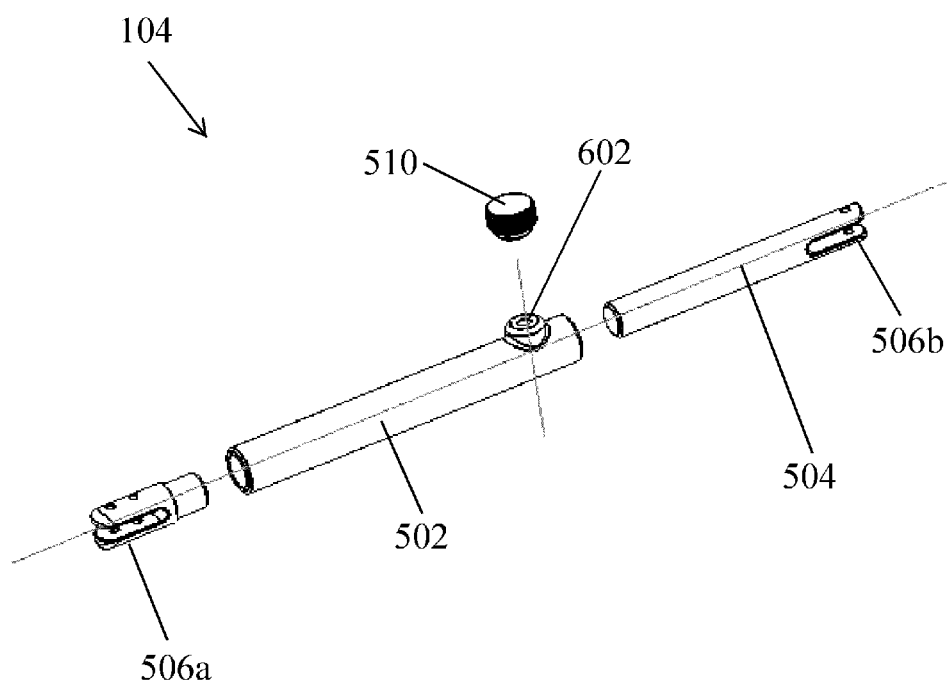
FIG. 7 is an exploded view of the adjustable linkage of FIG. 5.

As mentioned above, each surgical support frame can include a plurality of adjustable linkages 104a-c. FIGS. 5-7 illustrate one exemplary embodiment of an adjustable linkage (linkage 104 is shown to represent linkages 104a-c) of the present invention. As shown in FIG. 5, the adjustable linkage 104 has a telescoping rod assembly that includes a male rod section 504 that is slidably received within a lumen of a female rod section 502. Each rod section can include terminal ends 506a, 506b. The terminal ends 506a, 506b can have a variety of configurations to facilitate mating with the support members 106a-c. For example, the terminal end 506a can be a separate component mated to the female rod section 502, and the terminal end 506b can be formed as an integral part of the male rod section 504. Any combination of these integrated or modular end components can be used with either terminal end and such modifications are considered within the scope of the invention. In addition, any number of various mating shapes may be used for terminal ends 506a, 506b. For example, the terminal ends 506a, 506b can be jaw members as illustrated in FIG. 5, or can be ball-shaped features that are received in a complementary socket feature, as discussed below with respect to FIG. 18. Furthermore, the terminal ends 506a, 506b can be configured to mate to a support member in any of a fixed orientation (as shown by terminal end 506a having dual bores 512a, 512b to receive attachment pins or bolts) or an adjustable or pivotable orientation (as shown by terminal end 506*b* having a single bore 514 to receive a single attachment pin or bolt).

The adjustable linkage 104 can also include a locking mechanism 508 configured to lock the adjustable linkage at a desired length. The locking mechanism 508 can be implemented in a variety of manners known in the art. For example, the locking mechanism 508 can include a thumbscrew 510 extending through a threaded hole 602 formed in the female rod section 502, as shown in FIGS. 5-7. The distal end of thumbscrew 510 can press against the male rod section 504 to prevent the male rod section 504 from moving with respect to the female rod section 502. In other embodiments, the locking mechanism 508 can be implemented using electrically or pneumatically actuated components. Such embodiments can allow the simultaneous locking and unlocking of multiple adjustable linkages 104. These variations are all considered to be within the scope of the present invention.

Figure 8:
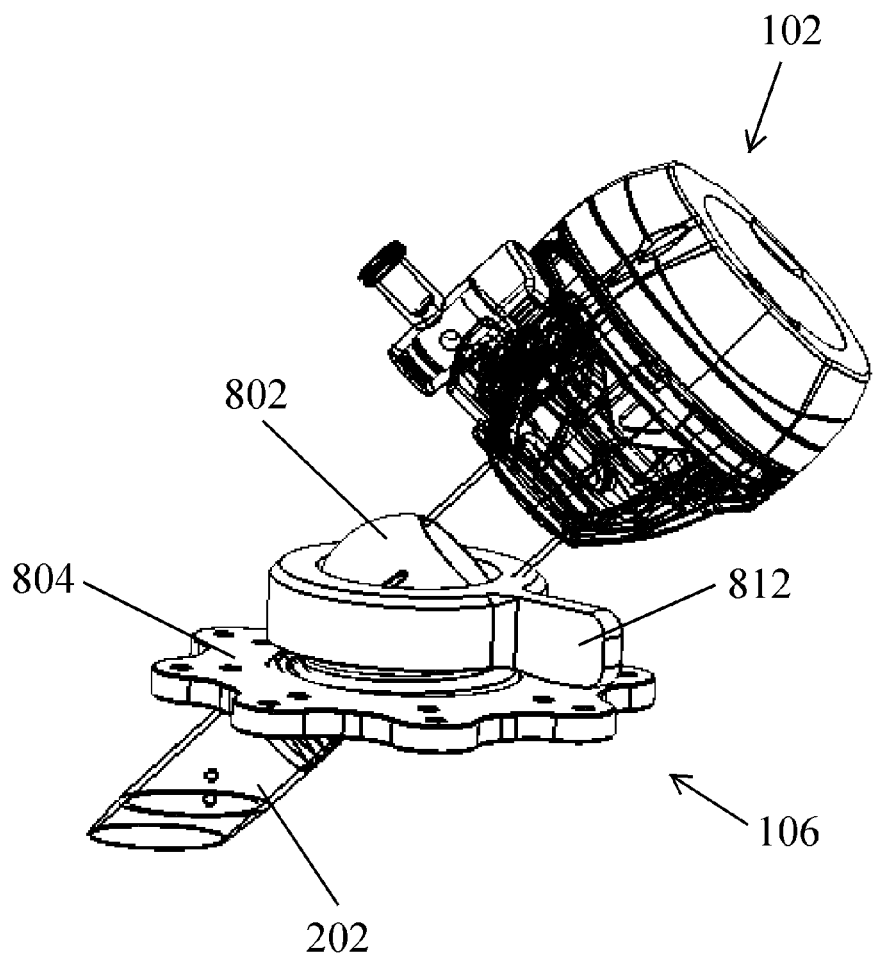
FIG. 8 is a perspective view of one embodiment of a support member of the surgical support frame of FIG. 1, shown retaining a trocar.
Figure 9:
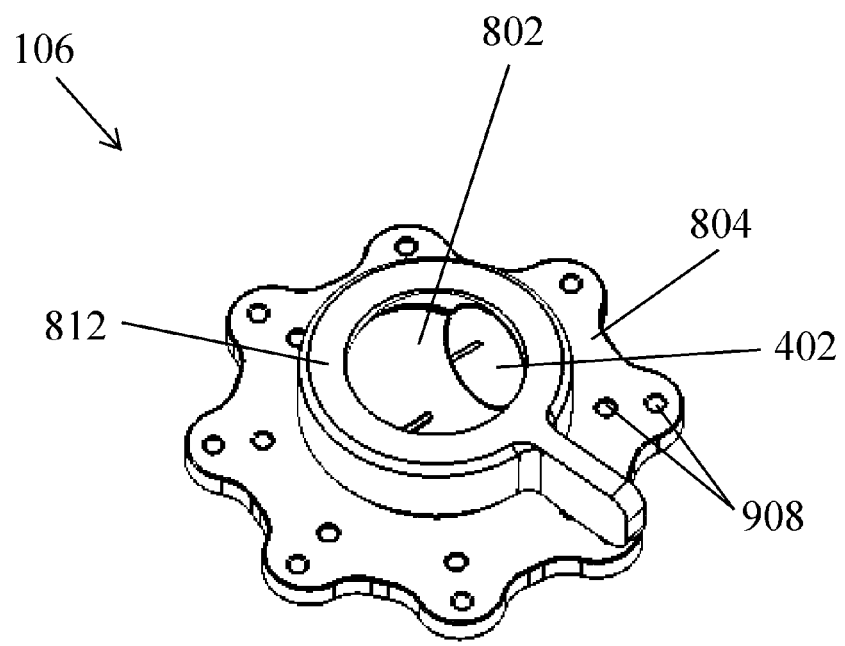
FIG. 9 is a top perspective view of the support member of FIG. 8 shown without a trocar.
Figure 10:
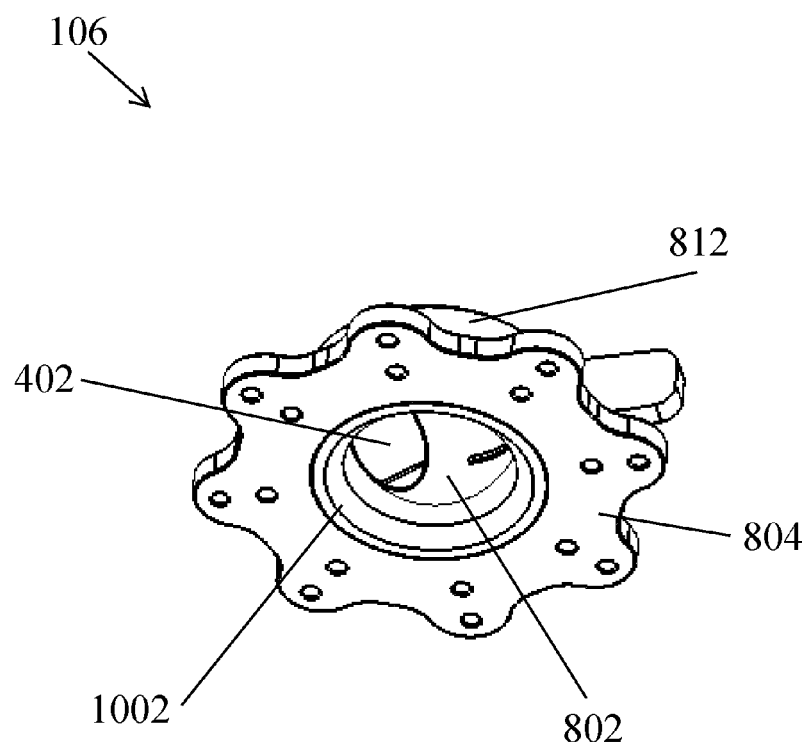
FIG. 10 is a bottom perspective view of the support member of FIG. 9.
Figure 11:
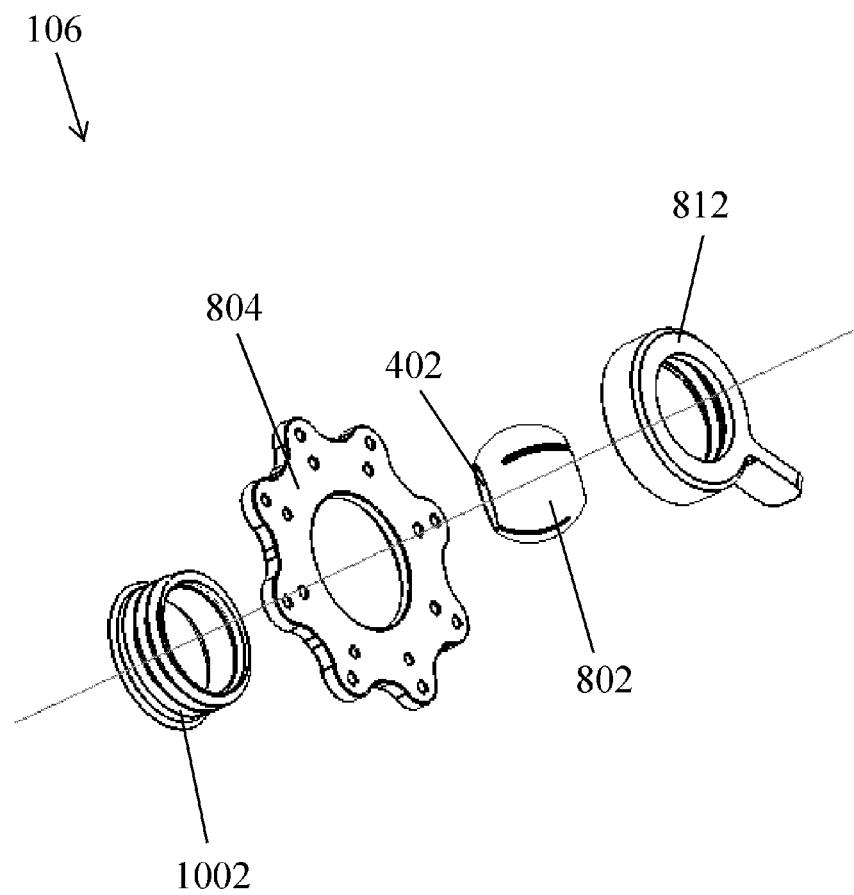
FIG. 11 is an exploded view of the support member of FIG. 9.

FIGS. 8-11 illustrate one exemplary embodiment of a support member (support member 106 is shown to represent supports 106*a-c*) of the present invention. As shown in FIG. 8, support member 106 can be configured to retain a trocar 102 in a desired orientation and/or position by receiving the distal trocar cannula (trocar cannula 202 is shown to represent cannulas 202*a-c*) through the support member 106. FIG. 9 illustrates the support member 106 without a trocar 102. While the support member 106 can have a variety of configurations, in an exemplary embodiment the support member 106 is in the form of a body having an opening therethrough for receiving a portion of an access device, such as a trocar cannula 102. The shape of the body can vary. By way of non-limiting example, in the illustrated embodiment the support member 106 has a generally circular shape with a substantially planar distal surface to allow positioning on a skin surface. As best shown in FIG. 11, the illustrated support member 106 generally includes a receiving member 1002, a receiving ball 802 polyaxially disposed within the receiving member 1002, and a cap 812 for retaining the ball 802 within the receiving member 1002. The ball 802 can have a lumen 402 extending therethrough for receiving the cannula. The support member 106 can also have a linking plate 804 disposed around the receiving member 1002 for mating with one or more of the telescoping linkages 104*a-c*. As a result of the receiving ball 802 being polyaxially disposed in the receiving member 1002, any cannula (e.g., trocar cannula 202) inserted through the receiving ball 802 will also be capable of moving polyaxially with respect to the receiving member 1002 and other components of the surgical support frame 100.

Figure 12:
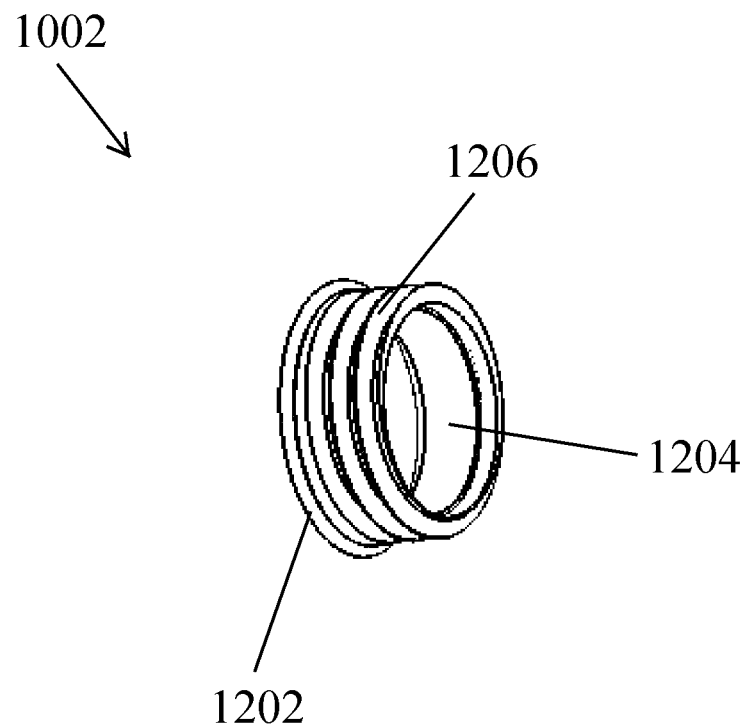
FIG. 12 is a perspective view of a receiving member of the support member of FIG. 9.

As shown in FIG. 12, the receiving member 1002 can form the base of the support member 106. The receiving member 1002 can have a substantially cylindrical shape with a flange 1202 formed on a terminal end thereof and configured to abut against a central lumen 1502 of the support member linkage plate 804 (shown in FIG. 15). The receiving member 1002 can define an inner lumen 1204 configured to house the receiving ball 802 without allowing the receiving ball to pass through the central lumen (e.g., the diameter of the inner lumen 1204 is smaller than the diameter of the receiving ball 802). The receiving member 1002 can also include threads 1206 formed on its outer surface and configured to interface with complementary threads 1402 formed on the inner surface of locking mechanism cap 812 (shown in FIG. 14).

Figure 13:
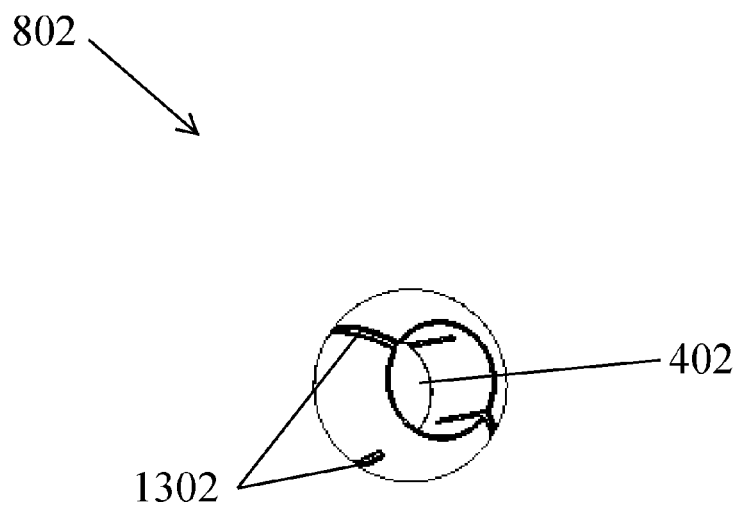
FIG. 13 is a perspective view of a receiving ball of the support member of FIG. 9.

The receiving ball 802, shown in isolation in FIG. 13, can have a generally spherical shape with a lumen 402 formed therethrough for receiving a trocar cannula 202. In addition, the receiving ball 802 can include one or more compression slots 1302 to allow the lumen 402 to adjust in diameter in response to actuation of the locking mechanism (e.g., locking mechanism cap 812). For example, compression slots 1302 that are generally coaxial to the lumen 402 can allow the receiving ball 802 (and lumen 402) to compress in response to pressure exerted on the ball by the locking mechanism. As the size of the lumen 402 decreases, a trocar cannula extending therethrough can be engaged by the ball 802 and fixed in a desired position such that it cannot rotate with respect to the support member 106 or translate through the lumen 402 formed in the support member.

Figure 14:
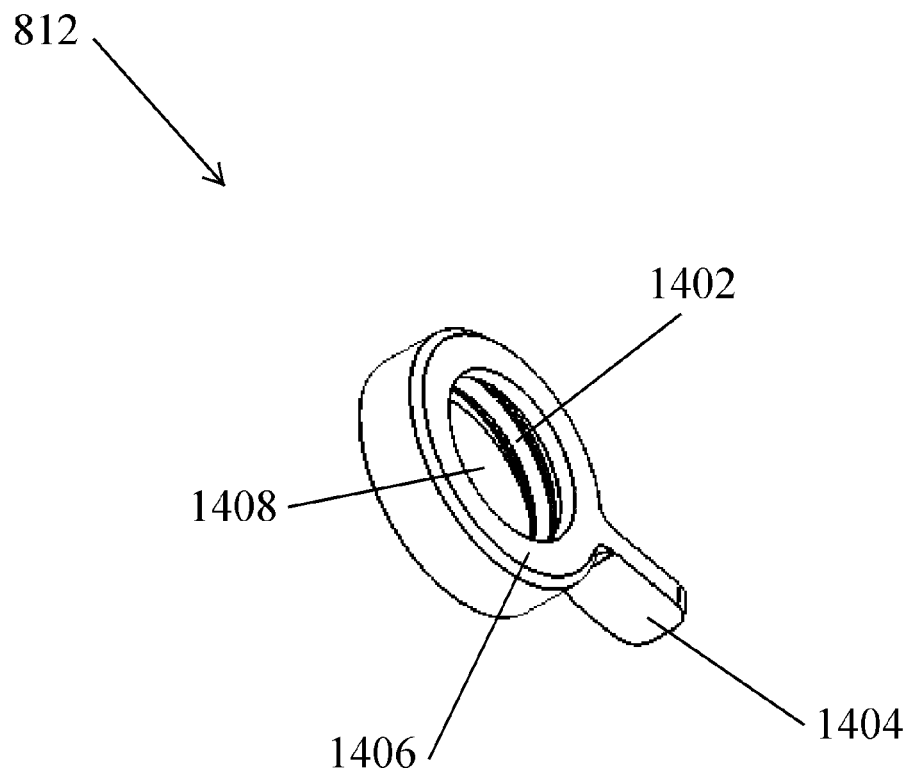
FIG. 14 is a perspective view of one embodiment of a locking mechanism of the support member of FIG. 9.

The support member 106 can also include a locking mechanism configured to retain the receiving ball 802 within the receiving member 1002 and to selectively restrain movement of the ball 802 relative to the receiving member 1002, thereby restraining the movement of any trocar cannula 202 disposed in the lumen 402 of the receiving ball 802. FIG. 14 illustrates one embodiment of a locking mechanism that is in the form of a threaded cap 812. As shown, the cap 812 can be ring-shaped with inner complementary threads 1402, a handle 1404 for manual actuation, and a flange 1406 with a central lumen 1408 configured to house the receiving ball 802 without allowing the receiving ball to pass through the central lumen 1408 (e.g., the diameter of the central lumen 1408 is smaller than the compressed diameter of the receiving ball 802, similar to the inner lumen 1204 of the receiving member 1002 described above). In this embodiment, as the cap 812 is threaded down onto the threads 1206 of the receiving member 1002, the flange 1406 abuts against the receiving ball 802 and compresses the ball against inner lumen 1204 of the receiving member 1002. Interference between the receiving ball 802, cap 812, and receiving member 1002 restrains the receiving ball—along with any cannula extending therethrough—from moving with respect to the support member. In other embodiments, the locking mechanism can be implemented with electrically or pneumatically actuated components, as will be discussed in detail below with respect to FIGS. 28A and 28B.

Figure 15:
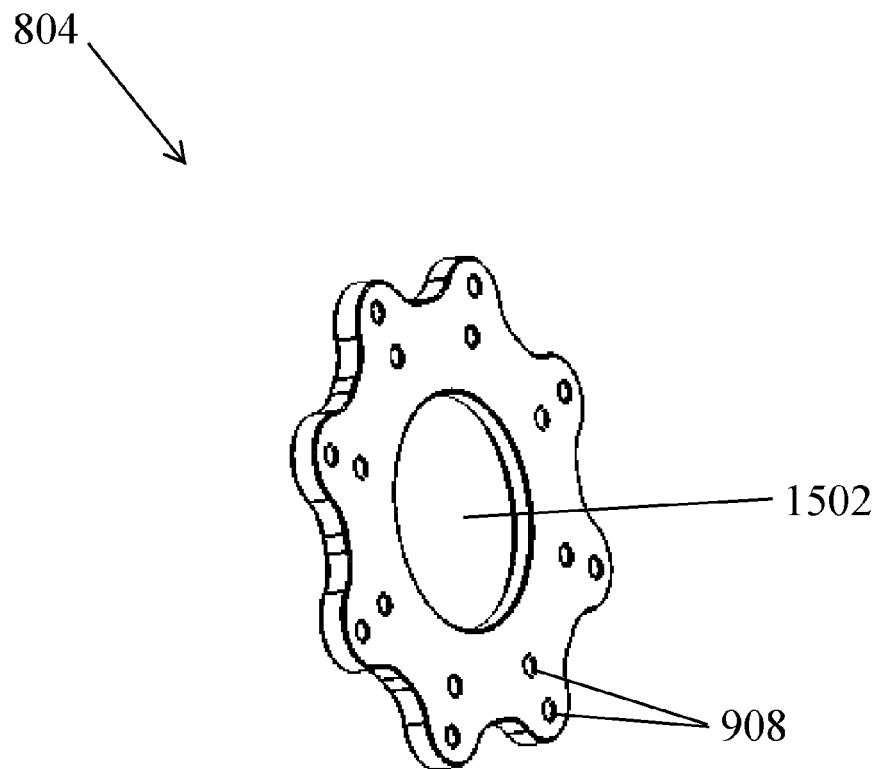
FIG. 15 is a perspective view of one embodiment of a linkage plate of the support member of FIG. 9.

FIG. 15 illustrates one embodiment of a support member linkage plate 804. The support member linkage plate 804 can be formed integrally with the receiving member 1002 or, in some embodiments, it can be disposed between the receiving member 1002 and the cap 812 to allow the support member 106 to be coupled to one or more linkages. The modular construction of the support member 106 facilitates easy disassembly for cleaning or replacement of broken components. The linkage plate 804 can have a variety of shapes and sizes to facilitate mating with a terminal end 506 of one or more of the adjustable linkages 104*a-c*. As shown in FIG. 15, the linkage plate 804 is generally ring-shaped and includes a plurality of attachment points 908 formed therein. The attachment points 908 can be in the form of depressions or other mating features formed on the surface of linkage plate 804, or can be in the form of bores formed therethrough for receiving an attachment pin or bolt. FIGS. 19-28, discussed in more detail below, illustrate other additional embodiments of attachment points 908.

Figure 16:
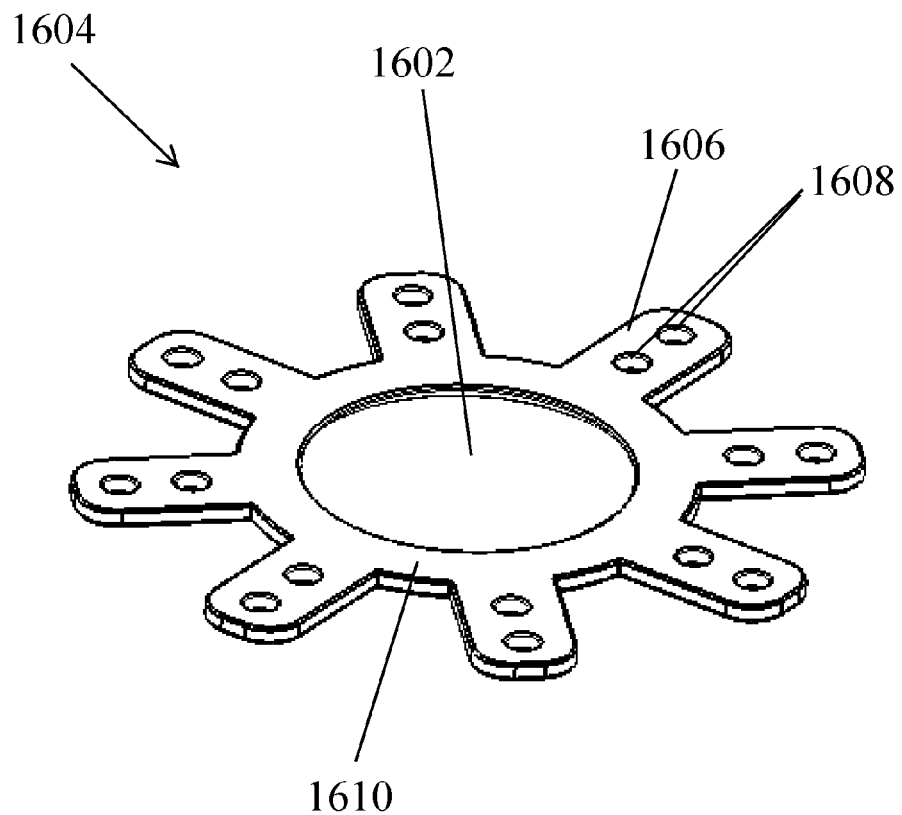
FIG. 16 is a perspective view of an alternative embodiment of a support member linkage plate of the present invention.

FIGS. 1-15 illustrate one embodiment of a surgical support frame of the present invention. Numerous variations of the illustrated embodiment are possible, all of which are considered to be within the scope of the present invention. For example, FIG. 16 illustrates an alternative embodiment of a support member linkage plate 1604 of the present invention. Linkage plate 1604 includes a central lumen 1602, similar to central lumen 1502 shown in FIG. 15. In this embodiment, however, the linkage plate 1604 has a plurality of attachment arms 1606 extending radially outward from a central ring portion 1610. Each attachment arm 1606 can have one or more attachment points 1608, similar to the attachment points 908 discussed above. A person skilled in the art will appreciate that a variety of other shapes are conceivable for use in the linkage plate 1604.

Figure 17:
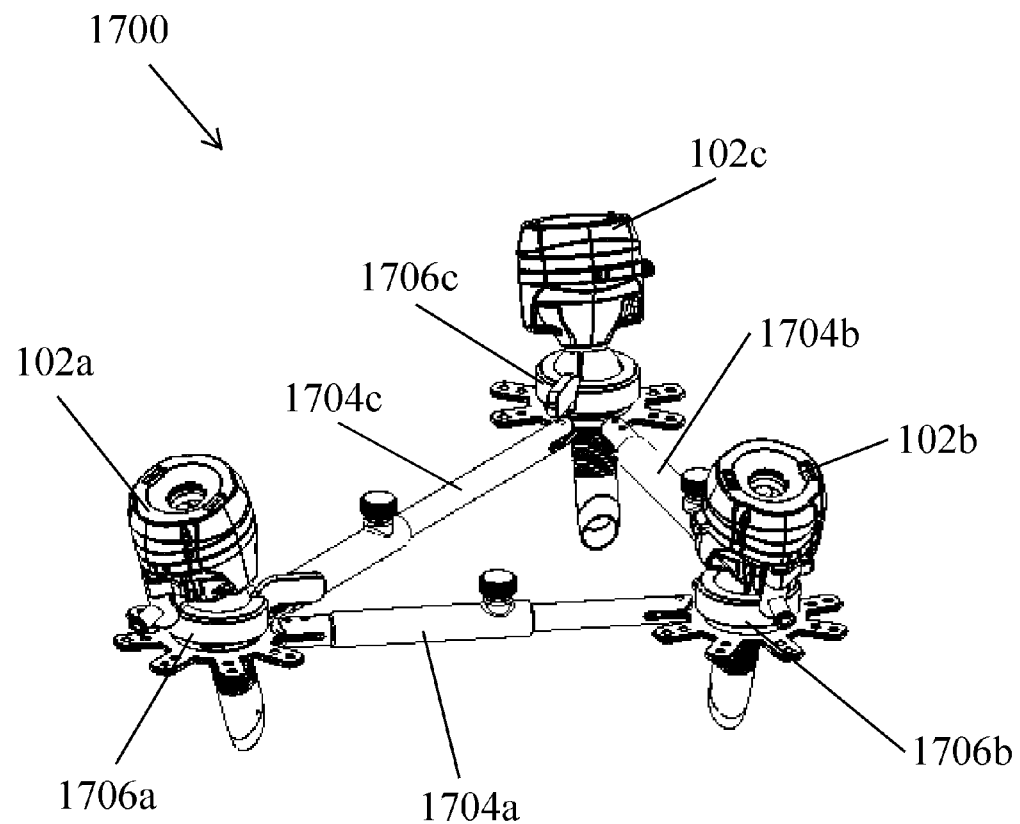
FIG. 17 is a perspective view of another embodiment of a surgical support frame of the present invention.

FIG. 17 illustrates another exemplary surgical support frame 1700 having adjustable linkages 1704a, 1704b, 1704c and support members 1706a, 1706b, 1706c that utilize the alternate support member linkage plate 1604 discussed above. Similar to the surgical support frame 100 shown in FIG. 1, surgical support frame 1700 can be used to support one or more trocars 102a, 102b, 102c in a desired orientation and/or position with respect to the body of a patient and any other trocars inserted through the frame.

Figure 18:
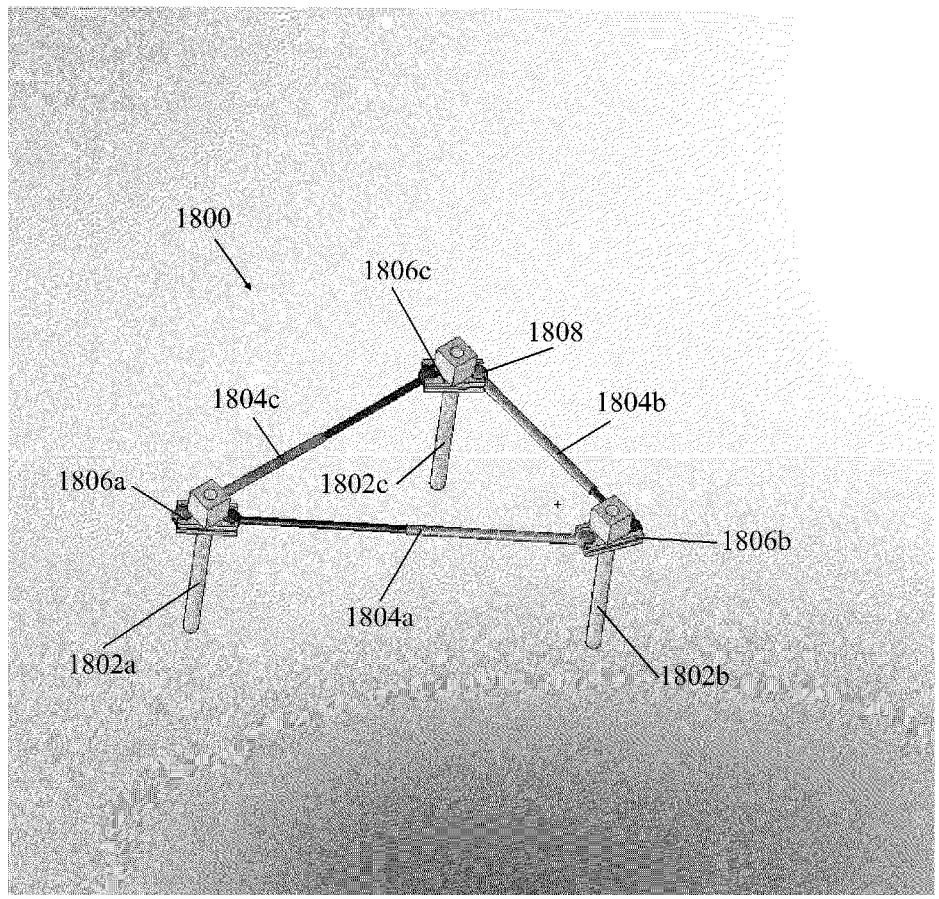
FIG. 18 is a perspective view of yet another embodiment of a surgical support frame of the present invention.

FIG. 18 illustrates another embodiment of a surgical support frame of the present invention. As shown, the surgical support frame 1800 is configured to support one or more trocars 1802a, 1802b, 1802c (or other cannulas for use in surgery) via a plurality of adjustable linkages 1804a, 1804b, 1804c and at least three support members 1806a, 1806b, 1806c. In this embodiment, the adjustable linkages 1804a-c and the support members 1806a-c are connected by ball-and-socket joints 1808. The ball-and-socket joints 1808 permit polyaxial angular adjustment of the entire support member, thus angularly orienting any cannula 1802a-c extending therethrough.

Both the adjustable linkages 1804a-c and the support members 1806a-c can include locking mechanisms to restrain the adjustment of the surgical support frame. For example, the adjustable linkages 1804a-c can include a locking mechanism similar to the locking mechanism 508 shown in FIG. 5 to prevent the adjustment of the length of any particular adjustable linkage 1804. Similarly, the support members 1806a-c can include a locking mechanism configured to restrain the motion of one or more of the ball-and-socket joints 1808. An exemplary locking mechanism can be implemented using a manually, electrically, or pneumatically actuated component (e.g., a threaded cap as described above) to increase friction between, for example, a ball formed on the terminal end of an adjustable linkage 1804 and a socket formed in a support member 1806.

Figure 19A:
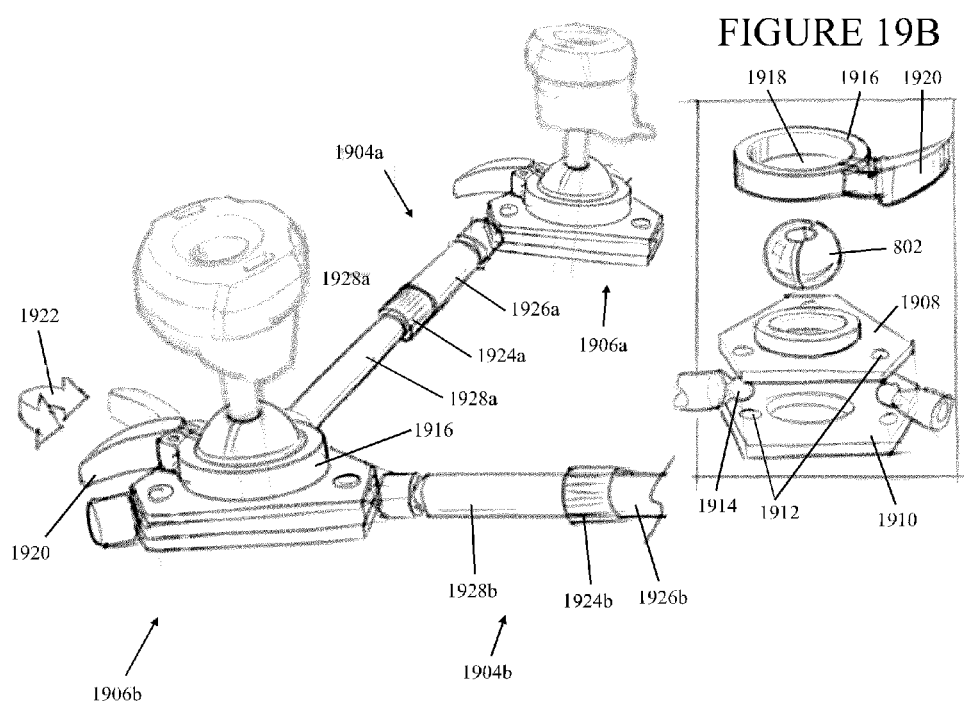
FIG. 19A is a perspective view of another embodiment of a surgical support frame including a collet locking mechanism.

FIG. 19A illustrates another embodiment of a surgical support frame having ball-and-socket joints that connect each adjustable linkage 1904a, 1904b to each support member 1906a, 1906b. As shown most clearly in FIG. 19B, a socket is formed by connecting a top linkage plate 1908 and a bottom linkage plate 1910 having bores 1912 formed therein such that a ball-shaped terminal end 1914 of an adjustable linkage 1904 can be received and sandwiched between the linkage plates. The linkage plates 1908, 1910 can be secured together using, for example, screws such that a set amount of pressure is applied to the ball-shaped terminal end of a linkage 1904. Alternatively, the linkage plates 1908, 1910 can be adjustable, e.g., using a thumbscrew, such that a user can selectively apply pressure to release or secure a ball-shaped terminal end 1914 with respect to the support member linkage plates.

The surgical support frame illustrated in FIGS. 19A and 19B also includes alternative embodiments of the support member and adjustable linkage locking mechanisms. As shown in the figures, the support member locking mechanism can be a ring-shaped collet 1916 fixed to one side of a top linkage plate 1908 using, for example, a screw. The collet 1916 can be sized to surround a receiving ball 802 without allowing the ball to pass through a lumen 1918 formed in the collet. The collet 1916 can include a cam lever 1920 that, when activated (e.g., moved as shown by the arrow 1922), tightens the ring-shaped collet around the receiving ball 802 so as to restrict its movement.

The adjustable linkage locking mechanism shown in FIG. 19A can include a threaded cap 1924 that receives an end of the female linkage member 1926 opposite a terminal end that is configured to mate to a support member 1906. The threaded cap 1924 can have a tapered threaded inner bore and the end of the female linkage member 1926 can have compression slots formed therein to allow compression of the female linkage member as the threaded cap is advanced on to the female linkage member. This compression can reduce the inner bore diameter of the female linkage member 1926, causing interference between the female linkage member 1926 and the male linkage member 1928 and preventing the adjustable linkage from telescoping.

Figure 20:
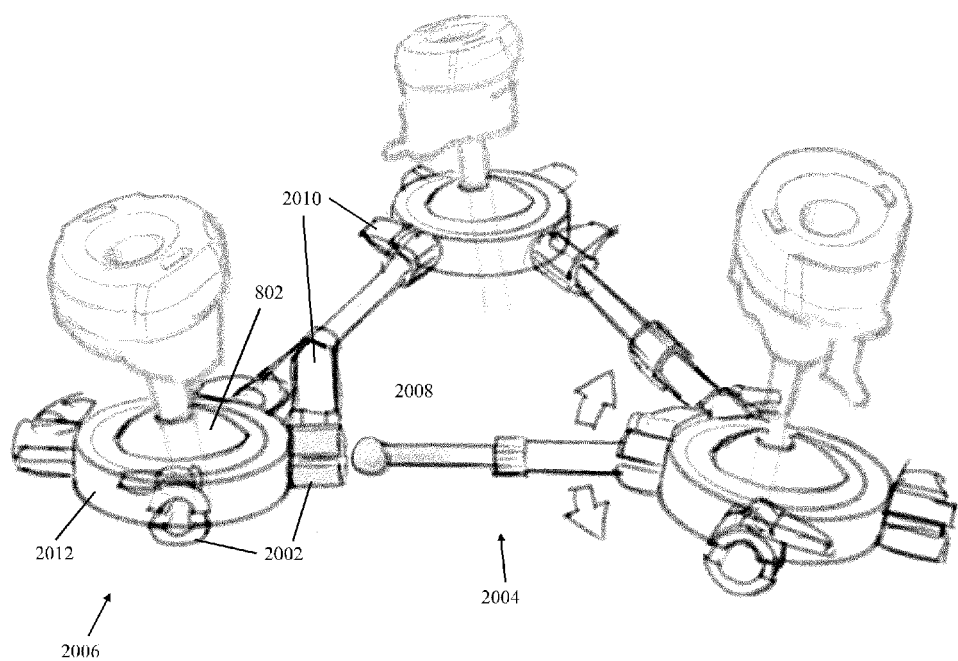
FIG. 20 is a perspective view of another embodiment of a surgical support frame including ball-and-socket linkage attachments.

FIG. 20 illustrates another embodiment of a surgical support frame utilizing ball-and-socket joints to link the support members and adjustable linkages. As shown in the figure, individual sockets 2002 can be formed at various locations around a support member 2006. These sockets 2002 can be configured to receive a ball-shaped terminal end 2008 of an adjustable linkage 2004. Each socket 2002 can also have an associated locking mechanism 2010 operable to restrict the movement of the ball-shaped terminal end 2008 within the socket. Locking mechanism 2010 can be, for example, a cam lever that, when actuated, compresses two halves of the socket 2002 together to cause interference with the ball-shaped terminal end 2008 and thereby restrict its movement.

FIG. 20 also shows an alternative embodiment of support member 2006 wherein a ring-shaped collet or other locking mechanism is integral with a support member body 2012. The support member body 2012 is configured to receive ball 802 and selectively restrict its movement when the locking mechanism is actuated.

Figure 21:
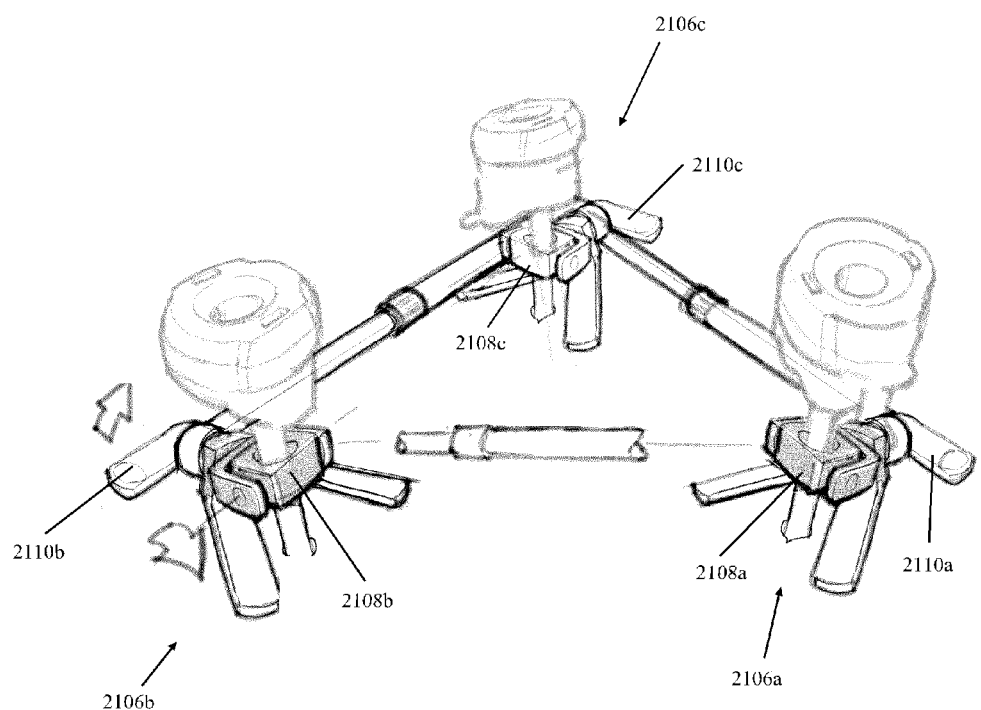
FIG. 21 is a perspective view of another embodiment of a surgical support frame including universal joint support members.

FIG. 21 illustrates still another embodiment of a support member 2106. In the illustrated embodiment, each support member 2106a, 2106b, 2106c includes a universal joint 2108a, 2108b, 2108c having a bore formed therethrough to accept a trocar cannula or other surgical device. Each universal joint 2108a-c can include a locking mechanism 2110a, 2110b, 2110c to fix the joint in a desired orientation. The locking mechanism 2110a-c can be configured to restrict one or more degrees of freedom of the universal joints 2108a-c. For example, and as shown in the figure, the locking mechanism 2110a-c can be a handle threaded on to a shaft that is also connected to the universal joint 2108a-c. As the threaded handle 2110a-c is tightened, it can cause interference with the universal joint 2108a-c, thereby restricting its ability to move in one or more directions.

Figure 22:
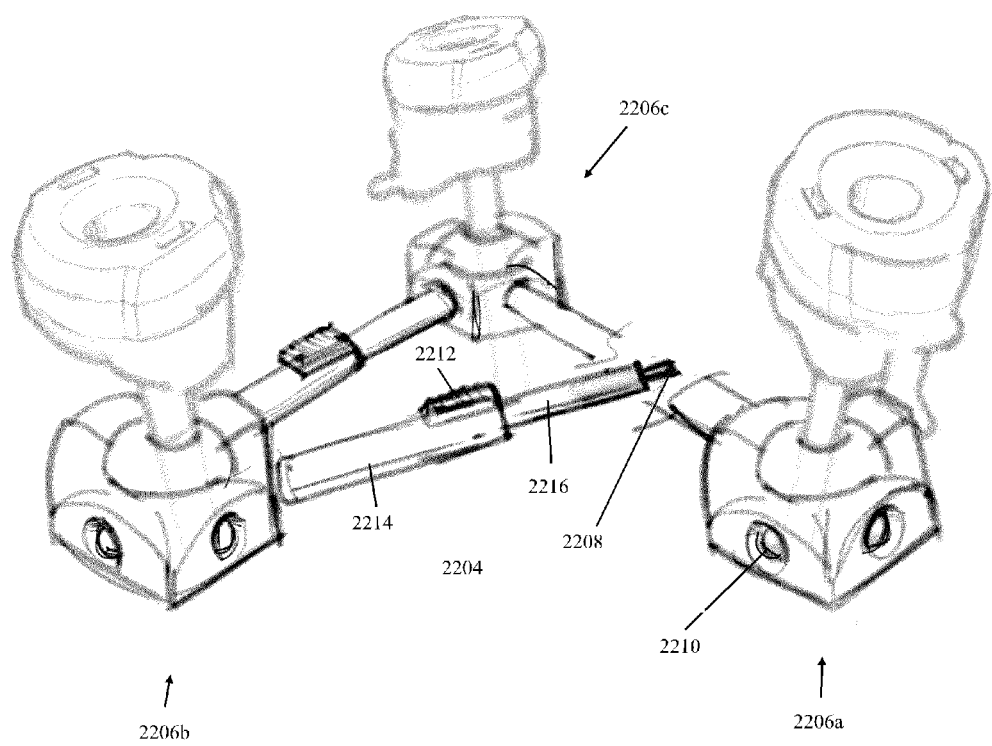
FIG. 22 is a perspective view of another embodiment of a surgical support frame including magnetic linkage attachments.

In other embodiments, one or more adjustable linkages can be connected to a support member using a magnetic coupling mechanism. As shown in FIG. 22, an adjustable linkage 2204 can include a magnetic terminal end 2208 configured to be received within a magnetic socket 2210 of a support member 2206a. The support members 2206a, 2206b, 2206c can include a plurality of magnet sockets 2210 at various locations to connect with one or more adjustable linkages 2204 in various orientations.

FIG. 22 also illustrates another embodiment of an adjustable linkage locking mechanism configured to lock the adjustable linkage 2204 at a desired length. As shown, the adjustable linkage 2204 can include a sliding tab 2212 configured to slide along the outer surface of the female linkage member 2214. The sliding tab 2212 can be further configured to cause interference between the female linkage member 2214 and the male linkage member 2216 when moved in one direction, and to provide clearance when moved in an opposing direction.

Figures 23A, 23B:
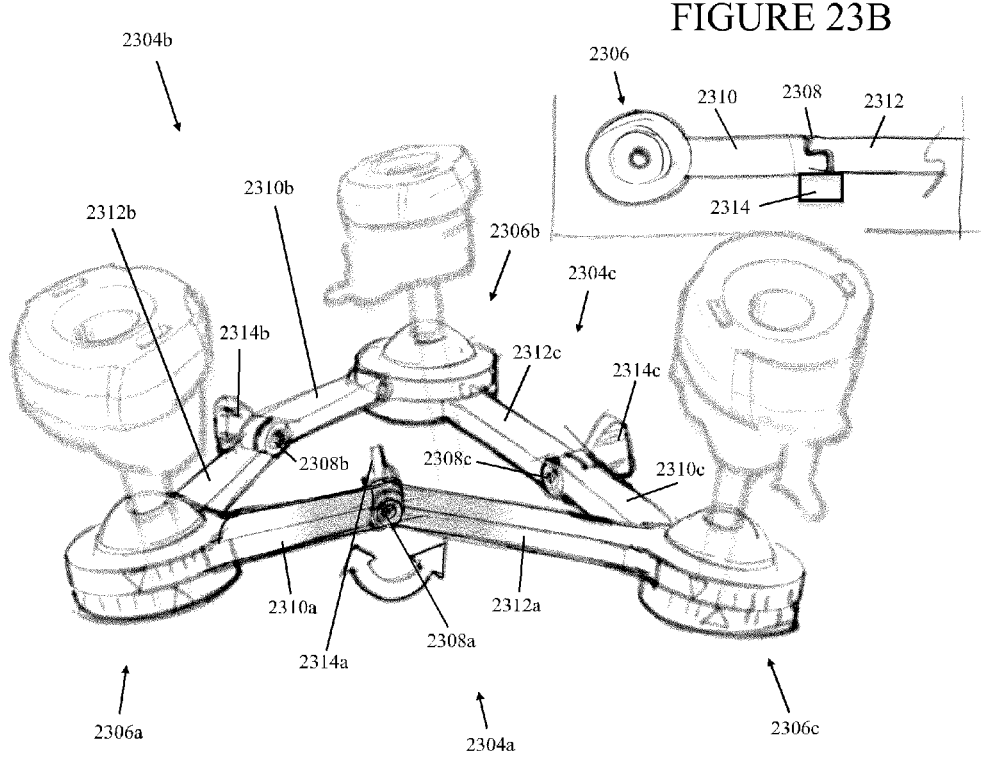
FIG. 23A is a perspective view of another embodiment of a surgical support frame including pivoting linkages.
FIG. 23B is a top view of an adjustable linkage of the surgical support frame in FIG. 23A.

In certain other embodiments, the adjustable linkages can be configured to provide adjustment other than to telescope in length. For example, FIG. 23A illustrates an embodiment of a surgical support frame in which the adjustable linkages 2304a, 2304b, 2304c include a first linkage section 2310a, 2310b, 2310c and a second linkage section 2312a, 2312b, 2312c with a pivot joint 2308a, 2308b, 2308c formed therebetween for allowing the first and second linkage sections to be angularly oriented relative to one another. Pivoting the first linkage sections 2310a-c with respect to the second linkage sections 2312a-c can also allow adjustment of the effective length of the linkages (i.e., the distance between the terminal ends of the linkages and, thus, any support members 2306a-c connected thereto). The adjustable linkages 2304a-c can include a locking mechanism associated with the joints 2308a-c to fix the linkages in a desired angular orientation. The locking mechanism can include a thumbscrew 2314a, 2314b, 2314c threaded through a bore formed in the first and second linkage sections 2310a-c, 2312a-c. As shown in the top view of FIG. 23B, the thumbscrew 2314 can be tightened to squeeze the first and second linkage sections 2310, 2312 together and cause interference, thereby fixing their orientation with respect to each other.

Figures 24A, 24B:
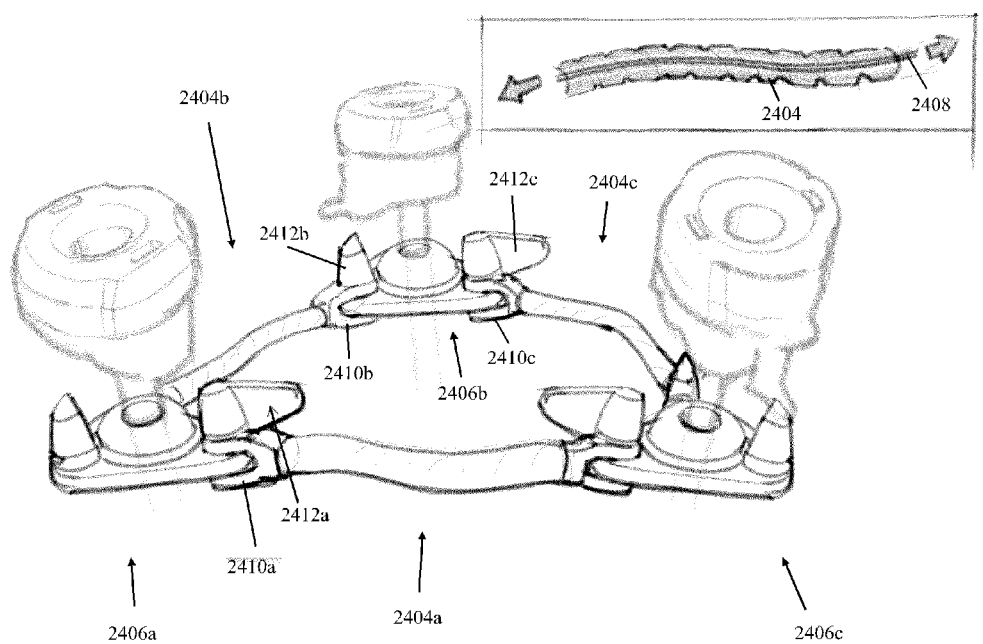
FIG. 24A is a perspective view of another embodiment of a surgical support frame including flexible adjustable linkages.
FIG. 24B is a side view of an adjustable linkage of the surgical support frame in FIG. 24A.
Figure 25:
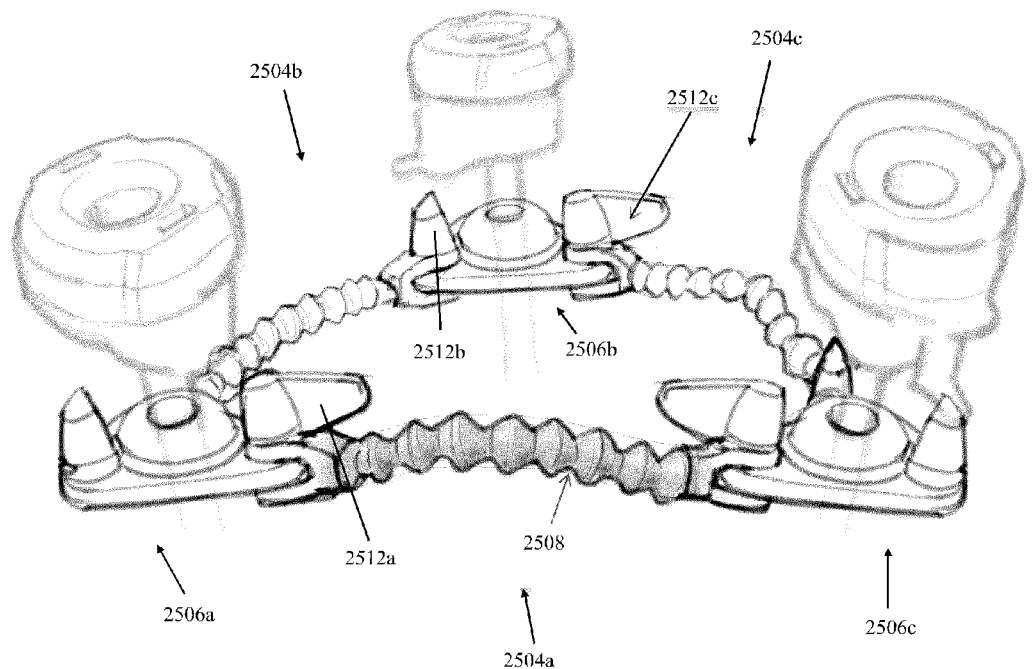
FIG. 25 is a perspective view of another embodiment of a surgical support frame including flexible adjustable linkages.

In still other embodiments, an adjustable linkage can be configured to provide even greater freedom of movement. FIGS. 24A, 24B, and 25 illustrate surgical support frames in which the adjustable linkages 2404a, 2404b, 2404c, 2504a, 2504b, 2504c can be adjusted to form a variety of shapes including straight, curved, and more. For example, the adjustable linkages 2404a-c in FIG. 24A can be formed from a coiled material or a plurality of linkage sections mated together. The linkages 2404a-c can also include a tensioning cable 2408 disposed within a central lumen of the adjustable linkage 2404, as shown in FIG. 24B. The tensioning cable 2408 can lock the adjustable member 2404 in a desired shape by squeezing each coil or linkage section together, thereby causing interference between them. A locking mechanism formed on a terminal end 2410a, 2410b, 2410c of the adjustable linkages 2404a-c can include a lever 2412a, 2412b, 2412c configured to both connect the terminal ends to support members 2406a, 2406b, 2406c and to tension any tensioning cables 2408 to lock the adjustable linkages 2404a-c in a desired shape.

FIG. 25 illustrates a similar embodiment in which the adjustable linkages 2504-c include a plurality of linkage sections 2508 connected together. Linkage sections 2508 can have unique complementary geometries as known in the art to facilitate friction locking to allow the adjustable linkages 2504a-c to retain a desired shape or orientation. Adjustable linkages 2508a-c can, in some embodiments, also include an inner tensioning cable and a lever 2512a, 2512b, 2512c configured to any of connect the adjustable linkages 2504a-c to support members 2506a-c and tension any tensioning cable, as discussed above.

Figure 26:
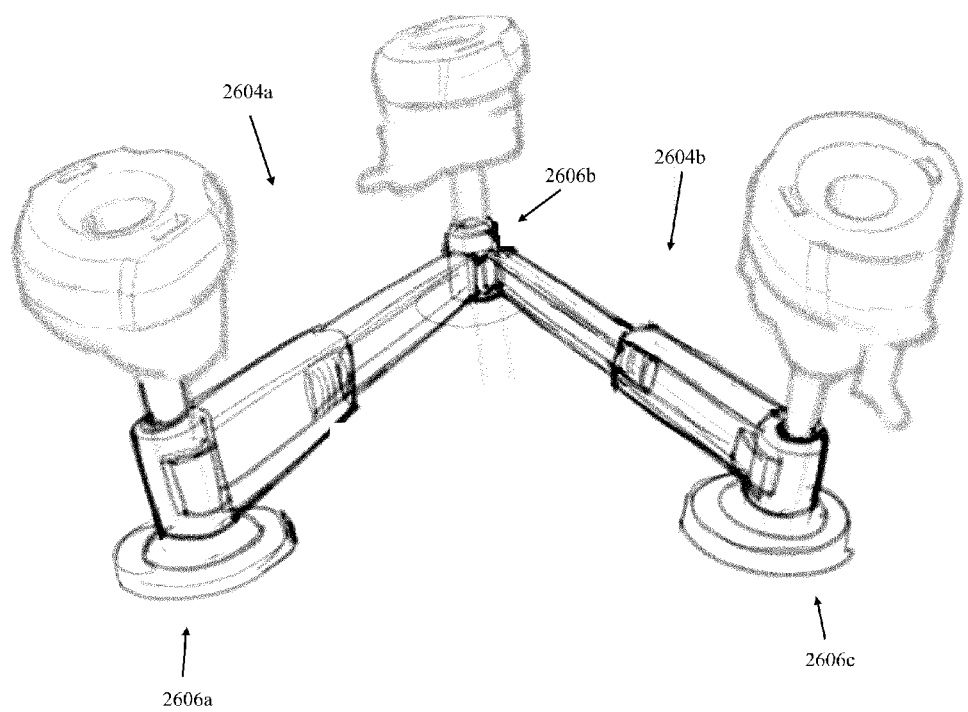
FIG. 26 is a perspective view of another embodiment of a surgical support frame including two rigid telescoping adjustable linkages.
Figure 27:
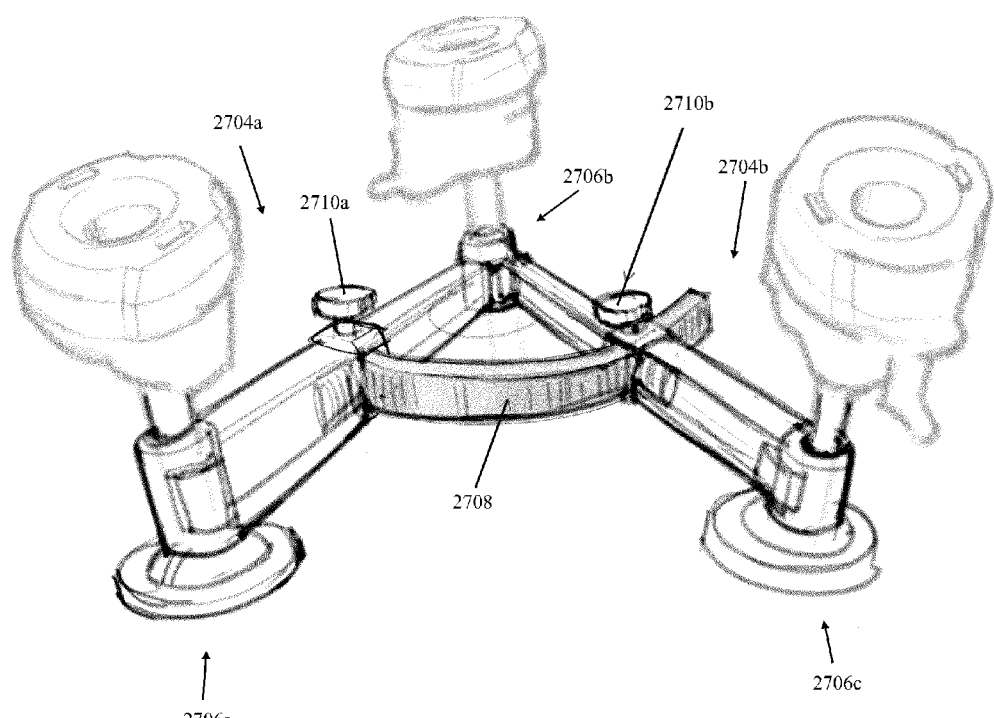
FIG. 27 is a perspective view of another embodiment of a surgical support frame including two telescoping linkages coupled to one another by a spread tie bar.

In some embodiments, a surgical support frame can be constructed including only two adjustable linkages to reduce the space required by the surgical support frame. An exemplary embodiment of such a surgical support frame is shown in FIG. 26. The illustrated surgical support frame includes a first adjustable linkage 2604a and a second adjustable linkage 2604b. The frame includes three support members 2606a, 2606b, 2606c at each terminal end of the adjustable linkages 2604a, 2604b. In order to maintain the structural integrity of the surgical support frame without a third adjustable linkage connecting support member 2606a to support member 2606c, the adjustable linkages 2604a-b can be rigidly connected to support members 2606a-c. Each adjustable linkage 2604a-b can telescope in length or otherwise adjust, as discussed above. In some embodiments, the adjustable linkages 2604a-b can include features to better support the weight of any devices disposed in the support members 2606a-c without a third adjustable linkage. In embodiments having telescoping adjustable linkages 2604a-b, these features can include square, I-beam, or other cross-sectional shapes capable of bearing the weight of the support members 2606a-c without deforming. In another embodiment shown in FIG. 27, the adjustable linkages 2704a, 2704b can include an additional connecting member 2708 extending between the adjustable linkages 2704a-b at a point along their length between their terminal ends. The connecting member 2708 can control the angle formed between the two adjustable linkages 2704a-b. In such an embodiment, the adjustable linkages 2704a-b can include a locking mechanism, such as a thumbscrew 2710a, 2710b that can be configured to selectively lock both the length of each adjustable linkage 2704a-b and the angle formed between the adjustable linkages.

Figures 28A, 28B:
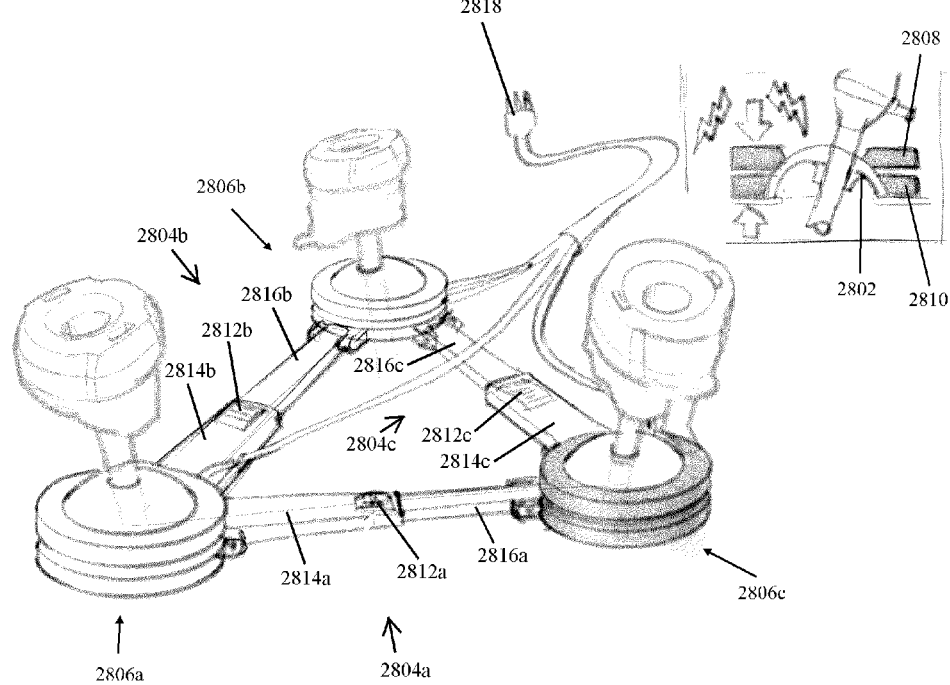
FIG. 28A is a perspective view of another embodiment of a surgical support frame including an electromagnetic locking mechanism.
FIG. 28B is a cross-sectional view of a support member of the surgical support frame of FIG. 28A.

In still other embodiments, the adjustable linkages can a rolling cam locking mechanism to selectively lock an adjustable linkage at a particular length. FIG. 28A illustrates a surgical support frame having adjustable linkages 2804a, 2804b, 2804c with this type of locking mechanism. As shown in the figure, adjustable linkages 2804a-c have a rectangular cross-sectional shape with a rolling locking mechanism 2812a, 2812b, 2812c. Each rolling locking mechanism 2812a-c can include a non-symmetrical rolling pin mounted on a female linkage member 2814a, 2814b, 2814c. The rolling pin can protrude into a male linkage member 2816a, 2816b, 2816c in one configuration, thereby restricting the movement of the male linkage member 2816a-c within the female linkage member 2814a-c. In another configuration, the rolling pin can provide clearance such that the male linkage member 2816a-c can telescope with respect to the female linkage member 2814a-c. By moving the rolling pin between the two configurations, each adjustable linkage 2804a-c can be selectively locked at a desired length.

FIG. 28A also illustrates another embodiment of a support member 2806a, 2806b, 2806c that includes an electrically actuated locking mechanism. As shown in the cross-sectional view of FIG. 28B, each support member 2806a-c includes a top electromagnetic plate 2808 and a bottom electromagnetic plate 2810. Upon application of a voltage from power source 2818, the electromagnetic plates 2808, 2810 can compress together causing interference with an inner receiving ball member 2802, thereby restricting its movement. Each support member 2806a-c can also include controlling components to selectively actuate the electromagnetic plates 2808, 2810, or a controller can be included separate from the device, as is known in the art. Other embodiments of the surgical support frame may make use of alternative actuation mechanisms. By way of example, pneumatically actuated pistons can be configured to press a cap (similar to cap 812 discussed above) or linkage plate (similar to linkage plates 2808, 2810) onto the receiving ball member 2802 to restrict its motion. Still further, a receiving member (similar to receiving member 1002 discussed above) can be configured to adjust in size in response to manual, electric, or pneumatic actuation, thereby restricting the movement of a receiving ball (similar to receiving ball 802 discussed above) disposed therein. Utilizing electric or pneumatic actuation technologies can also allow for simultaneous locking and unlocking of multiple support members. All of these variations are considered within the scope of the present invention.

The embodiments described above provide devices capable of, for example, fixing a trocar cannula in a desired location and/or orientation with respect to one or more other trocars and the body of a patient. The surgical support frame of the present invention can also include devices configured to secure a surgical instrument extending through a trocar into the body of a patient. Using such a device, the surgical support frame can be configured to retain both the trocar and any surgical device inserted therethrough in a fixed orientation with respect to any other trocar or surgical device and the body of a patient. FIGS. 29A, 29B, and 29C illustrate an exemplary device for fixing a surgical instrument with respect to a surrounding trocar. As shown in FIG. 29A, the locking device 2902 includes a body 2904 having a central lumen 2906 configured to align with a central lumen of a trocar. The locking device 2902 also includes a lever 2908 configured to fix any surgical instrument extending through the central lumen 2906 with respect to the locking device 2902. The locking device 2902 can further include one or more attachment clips 2910 with one or more release buttons 2912 configured to move the one or more clips 2910.

As shown in FIG. 29B, the locking device 2902 is in the form of a cap or housing that is configured to attach to the top of a surgical trocar, such as trocar 102 shown in FIG. 1. The one or more clips 2910 are configured to engage with one or more complementary slots formed on the top surface of the trocar 102. When in position, the central lumen 2906 of the locking device 2902 is in alignment with a central lumen of the trocar 102. To remove the locking device 2902, the one or more release buttons 2912 can be depressed to move the one or more clips 2910 and cause their release from the one or more complementary slots formed on the top surface of the trocar 102.

When the locking device 2902 is disposed on top of a trocar and a surgical instrument is inserted through the central lumen 2906, the lever 2908 can be used to fix the surgical instrument with respect to the locking device 2902 and the trocar. FIG. 29C illustrates an exemplary mechanism for fixing a surgical instrument with respect to the locking device 2902. As shown in the figure, lever 2908 pivots around an attachment pin 2914 and includes a shelf 2916 configured to push against a locking tab 2918 when the lever 2908 is pushed into the orientation shown in FIG. 29A. In response to the pressure from shelf 2916, locking tab 2918 can extend into the central lumen 2906 and press any surgical instrument disposed therethrough into the opposite wall 2920 of the central lumen 2906. When the lever 2908 is returned to the orientation shown in FIG. 29C, the shelf 2916 is rotated away from the locking tab 2918 (which can be spring loaded to retreat from the central lumen 2906) which allows the surgical instrument disposed through the central lumen 2906 to move freely.

The surgical support frame of the present invention can be manufactured using a variety of materials. For example, the surgical support frame can be manufactured using various metals such as titanium or titanium alloys. In addition, the surgical support frame can be manufactured using any of a variety of polymers. In certain embodiments, surgical support frames constructed from biocompatible metals, polymers, or combinations thereof are preferred. Similarly, the surgical support frame of the present invention can be constructed in a variety of sizes. The size of the surgical support frame, and the magnitude of adjustment possible in components such as the adjustable linkages, can be varied according to intended use and user desire. In some embodiments, surgical support frames sized to rest stably on a human torso and provide adjustable access to various locations on a human torso are preferred.

In another aspect of the invention, methods of using a surgical support frame of the present invention are provided. In one embodiment, a surgeon or other user can position a surgical support frame on a skin surface of a patient. For example, a surgeon can position a surgical support frame on top of the stomach of a patient when the patient is lying supine in an operating room. The surgeon can optionally be provided with a kit of support members and linkages, allowing the surgeon to construct a support frame having the desired number of supports at desired locations.

The surgeon or other user can manipulate a first surgical instrument extending through a first cannula that is mounted on the surgical support frame to position a distal end of the first surgical instrument within a body cavity. With the surgical instrument is in a desired position, the surgeon can lock the first cannula in a fixed position and/or orientation relative to the support frame, thereby locking the cannula in a fixed orientation relative to the body of the patient. The surgeon can also manipulate a second surgical instrument extending through a second cannula mounted on the surgical support frame to position a distal end of the second instrument within a body cavity. Following positioning of one or more surgical instruments, the surgeon or other user can lock at least one of the first and second cannulas in a fixed position and/or orientation relative to the support frame such that at least one of the first and second surgical instruments is maintained in a desired fixed position. Having locked one or more of the first and second surgical instruments in a fixed position and/or orientation with respect to each other and the patient, the surgeon or other user can manipulate a third surgical instrument extending through a third cannula mounted on the surgical support frame to position a distal end of the third surgical instrument within a body cavity. This process can be repeated for as many support members as the frame may have. By providing the surgeon or other user with a way to secure the position and/or orientation of one or more surgical instruments, the surgical support frame of the present invention allows the surgeon to more efficiently control the various instruments required during a laparoscopic procedure without the need for additional surgeons, assistants, etc.

In another aspect of the invention, a surgeon or other user can position a surgical support frame of the present invention on a skin surface of a patient (e.g., on the stomach or torso of a patient). The surgeon can then move at least one of the support members of the surgical support frame to adjust an effective length (i.e., a length between the terminal ends of the adjustable member) of at least one of the adjustable linkages of the surgical support frame. Adjusting the effective length of one or more of the adjustable linkages can allow the surgeon to position one or more surgical instruments at one or more desired locations on the skin surface of the patient and, accordingly, at one or more desired locations within a body cavity of the patient. The surgeon or other user can also or alternatively angularly adjust at least a portion of at least one of the support members of the surgical support frame relative to the connected telescoping linkages. For example, a cannula extending through the support can be angularly adjusted to thereby cause either a ball through which the cannula is disposed to move polyaxially, or to cause the entire support member to pivot or angulate relative to the linkages coupled thereto. Angularly orienting the support members can further aid in positioning one or more surgical instruments at one or more desired locations on the skin surface of the patient and/or within a body cavity of the patient.

Following or during positioning of the various support members of the surgical support frame, the surgeon or other user can lock at least one of the adjustable linkages to retain the selected effective length of the linkage. In addition, the surgeon or other user can lock at least one of the support members to retain the selected angular orientation of the support member or cannula or instrument extending therethrough. By locking the adjustable linkages and support members in a desired position, the surgical support frame can retain one or more cannulas (e.g., surgical trocars) and/or surgical instruments in a desired position and/or orientation relative to each other instrument inserted through the frame. Furthermore, because the surgical support frame rests on a patient, the surgical devices are also held in a fixed position and/or orientation with respect to the body of the patient.

The devices disclosed herein can be designed to be disposed after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A surgical support frame, comprising:
at least three support members connected to one another by at least three independently adjustable linkages arranged around a perimeter of an enclosed shape, each support member having a lumen extending therethrough for receiving a cannula, and each support member being configured such that a cannula extending through one of the at least three support members can be locked in a transverse angular orientation relative to a cannula extending through another one of the at least three support members, and such that a distance between each of the at least three support members is independently adjustable.

2. The surgical support frame of claim 1, further comprising a locking mechanism associated with at least one of the at least three support members for locking at least one of the at least three support members such that a cannula extending through one of the at least three support members is retained in a desired angular orientation relative to a cannula extending through another one of the at least three support members.

3. The surgical support frame of claim 1, wherein each support member is movably connected to at least one of the at least two adjustable linkages by ball and socket joints.

4. The surgical support frame of claim 1, wherein the at least three support members comprise first, second, and third support members, and wherein the adjustable linkages are arranged to define a perimeter of a triangle.

5. The surgical support frame of claim 1, wherein the at least three support members comprise first, second, third, and fourth support members, and wherein the adjustable linkages are arranged to define a perimeter of a square.

6. The surgical support frame of claim 1, further comprising a locking mechanism associated with at least one of the at least two adjustable linkages for locking at least one of the at least two adjustable linkages at a desired length.

7. A surgical support frame, comprising:
first, second, and third support members, each having a lumen extending therethrough that defines a central axis, and each support member being configured such that the orientation of the central axis of the lumen is adjustable relative to the central axis of the lumen of another one of the support members;
a first linkage rod extending from the first support member directly to the second support member;
a second linkage rod extending from the second support member directly to the third support member; and
a third linkage rod extending from the first support member directly to the third support member,
wherein at least one of the first, second and third support members includes a locking mechanism configured to retain the central axis of the lumen of the support member in a desired orientation relative to the central axis of the lumen of another one of the support members.

8. The surgical support frame of claim 7, wherein a length of each of the first, second, and third linkage rods can be adjusted.

9. The surgical support frame of claim 8, wherein at least one of the first, second, and third linkage rods includes a locking mechanism configured to lock the respective linkage rod at a desired length.

10. A surgical support frame, comprising:
at least three support members connected to one another by at least two adjustable linkages, each support member having a receiving member, a cap, and a receiving ball disposed between the receiving member and the cap such that the receiving ball can move poliaxially relative to the support member,
wherein the receiving ball includes a lumen formed therein for receiving a cannula, and wherein the cap is configured to move relative to the receiving member to selectively inhibit the poliaxial movement of the receiving ball, and
wherein a length along a longitudinal axis of each adjustable linkage extending between proximal and distal ends thereof can be adjusted.

11. The surgical support frame of claim 10, wherein the surgical support frame comprises at least three adjustable linkages and wherein the at least three adjustable linkages are arranged to define a perimeter of an enclosed shape.

12. The surgical support frame of claim 11, wherein the at least three support members comprise first, second, and third support members, and wherein the adjustable linkages are arranged to define a perimeter of a triangle.

13. The surgical support frame of claim 10, further comprising a locking mechanism associated with at least one of the at least two adjustable linkages for locking at least one of the at least two adjustable linkages at a desired length.

* * * * *